United States Patent
Cheng et al.

(10) Patent No.: US 9,850,219 B1
(45) Date of Patent: *Dec. 26, 2017

(54) PHENOTHIAZINE DERIVATIVES AND METHODS OF USE THEREOF

(71) Applicant: Acenda Pharma, Inc., Coral Springs, FL (US)

(72) Inventors: Haiyung Cheng, Coral Springs, FL (US); Chi-Feng Lin, Taipei (TW); Jhen-Hua Shih, Taipei (TW); Alexander C. H. Wu, Taipei (TW)

(73) Assignee: Acenda Pharma, Inc., Coral Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,118

(22) Filed: Jun. 16, 2017

Related U.S. Application Data

(63) Continuation of application No. 15/295,769, filed on Oct. 17, 2016, now Pat. No. 9,695,138.

(51) Int. Cl.
| | | |
|---|---|---|
| *C07D 279/26* | (2006.01) | |
| *A61K 33/24* | (2006.01) | |
| *A61K 31/5377* | (2006.01) | |
| *A61K 45/06* | (2006.01) | |
| *A61K 31/5415* | (2006.01) | |

(52) U.S. Cl.
CPC ........ *C07D 279/26* (2013.01); *A61K 31/5377* (2013.01); *A61K 31/5415* (2013.01); *A61K 33/24* (2013.01); *A61K 45/06* (2013.01)

(58) Field of Classification Search
None
See application file for complete search history.

(56) References Cited

U.S. PATENT DOCUMENTS

| | | |
|---|---|---|
| 2,902,484 A | 9/1959 | Horclois |
| 6,054,453 A | 4/2000 | Lohray et al. |
| 6,440,961 B1 | 8/2002 | Lohray et al. |
| 6,548,666 B1 | 4/2003 | Lohray et al. |
| 6,608,194 B1 | 8/2003 | Lohray et al. |
| 7,060,708 B2 | 6/2006 | Piccariello et al. |
| 7,427,600 B2 | 9/2008 | Mickle et al. |
| 8,394,813 B2 | 3/2013 | Mickle et al. |
| 8,846,021 B2 | 9/2014 | Charles |
| 9,132,134 B2 | 9/2015 | De Colle et al. |
| 9,695,138 B1 * | 7/2017 | Cheng ................ C07D 279/26 |
| 2004/0063628 A1 | 4/2004 | Piccariello et al. |
| 2005/0080075 A1 | 4/2005 | Nichols et al. |
| 2007/0060500 A1 | 3/2007 | Mickle et al. |
| 2007/0232529 A1 | 10/2007 | Mickle et al. |
| 2009/0253792 A1 | 10/2009 | Mickle et al. |
| 2010/0035858 A1 | 2/2010 | Roth et al. |
| 2010/0130457 A1 | 5/2010 | Roth et al. |
| 2010/0166700 A1 | 7/2010 | Charles |
| 2012/0046279 A1 | 2/2012 | Gu et al. |
| 2013/0337534 A1 | 12/2013 | Charles |
| 2014/0038886 A1 | 2/2014 | Mier et al. |
| 2014/0294994 A1 | 10/2014 | Huang |
| 2015/0050714 A1 | 2/2015 | Charles |
| 2015/0087638 A1 | 3/2015 | De Colle et al. |
| 2015/0342958 A1 | 12/2015 | De Colle et al. |

FOREIGN PATENT DOCUMENTS

| | | |
|---|---|---|
| EP | 1357928 | 11/2011 |
| FR | 6596 | 1/1969 |
| GB | 2371983 A | 8/2002 |
| WO | WO 1994/023726 | 10/1994 |
| WO | WO 2000/050414 | 8/2000 |
| WO | WO 2002/098949 | 12/2002 |
| WO | WO 2003/020200 | 3/2003 |
| WO | WO 2007/100902 | 9/2007 |
| WO | WO 2010/009332 | 1/2010 |
| WO | WO 2010/056979 | 5/2010 |
| WO | WO 2012/107579 | 8/2012 |
| WO | WO 2013/060305 | 5/2013 |
| WO | WO 2014/105655 | 7/2014 |
| WO | WO 2015/135947 | 9/2015 |
| WO | WO 2015/184794 | 12/2015 |

OTHER PUBLICATIONS

Roberts et al. "Chemistry for peptide and protein PEGylation", Advanced Drug Delivery Reviews, 2002, vol. 54, p. 459-476.

Yeh et al. "Trifluoperazine, an Antipsychotic Agent, Inhibits Cancer Stem Cell Growth and Overcomes Drug Resistance of Lung Cancer", American Journal of Respiratory and Critical Care Medicine, (2012), vol. 186, p. 1180-1188.

* cited by examiner

*Primary Examiner* — Brian J Davis
(74) *Attorney, Agent, or Firm* — Cooley LLP; Heidi A. Erlacher; Christine C. Pemberton

(57) ABSTRACT

The present disclosure relates to phenothiazine derivatives such as conjugates of phenothiazine compounds, as well as pharmaceutical compositions thereof. The present disclosure also relates to a method of making and the use of such compounds for treating cancer, e.g., a lung cancer, a colon cancer, breast cancer or pancreatic cancer.

20 Claims, No Drawings

PHENOTHIAZINE DERIVATIVES AND METHODS OF USE THEREOF

RELATED APPLICATIONS

This application is a continuation application of U.S. application Ser. No. 15/295,769, filed Oct. 17, 2016 (now allowed), the content of which is incorporated herein by reference in its entirety.

BACKGROUND

Most patients with non-small cell lung cancer (NSCLC) have an inoperable disease that requires systemic therapy. Resistance to chemotherapy, e.g., epidermal growth factor receptor-tyrosine kinase inhibitor (EGFR-TKI), is a major problem for treating systemic NSCLC. For instance, chemotherapy resistance can be explained by cancer stem-like cell (CSC) theory. CSCs have been shown to possess stem cell characteristics, e.g., self-renewal, enhanced migration, and stress and drug resistance, all of which have been implicated in cancer recurrence and cancer metastasis (Yeh et al., *Am. J. Respir. Crit. Care Med.* 186, 1180 (2012)). New drugs are needed for cancer treatment.

SUMMARY

In one aspect, the present disclosure features a phenothiazine compound of Formula (I):

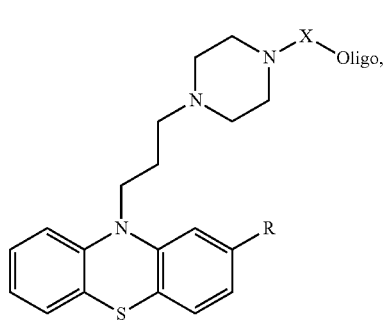

(I)

or a pharmaceutically acceptable salt thereof, wherein:

Oligo is an oligomer or a co-oligomer selected from the group consisting of —[CH$_2$CH(OR$^1$)CH$_2$O]$_m$—R$^2$, —[CH$_2$CH$_2$O]$_n$—R$^3$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$;

R is H, halo, C$_1$-C$_4$ alkyl substituted with one or more halo, or —S—C$_1$-C$_4$ alkyl;

each of R$^1$, R$^2$ and R$^3$ independently is H or C$_1$-C$_4$ alkyl;

X is a bond, C(O), C(O)O, or C(O)CH$_2$O;

m is an integer ranging from 2 to 16, and n is an integer ranging from 3 to 16, and when Oligo is —[CH$_2$CH$_2$O]$_n$—R$^3$, in which n is 12 or 13 and R$^3$ is methyl, then X is C(O), C(O)O, or C(O)CH$_2$O.

In certain embodiments, the compounds of Formula (I) are cytotoxic to human NSCLC cells, e.g., H441GL (ATCC® HTB-174™), A549 (ATCC® CCL-185™) or H1299 (ATCC® CCL-5803™).

In certain embodiments, the compounds of Formula (I) are inhibitors of NSCLC cells with an IC$_{50}$ value from about 15 μM or less, about 10 μM or less, about 5 μM or less, about 1 μM or less, about 500 nM or less, about 300 nM or less, about 200 nM or less, about 100 nM or less, about 50 nM or less, about 25 nM or less, about 10 nM or less, about 5 nM or less, or about 1 nM or less.

In certain embodiments, the compounds of Formula (I) are cytotoxic to human cancer cells, e.g., HCT116, DLD1, MCF7, MDA-MB-231, PANC-1 or SUIT-2.

In certain embodiments, the compounds of Formula (I) are inhibitors of human cancer cells (e.g., colon cancer cells, breast cancer cells and pancreatic cancer cells) with an IC$_{50}$ value from about 15 μM or less, about 10 μM or less, about 5 μM or less, about 1 μM or less, about 500 nM or less, about 300 nM or less, about 200 nM or less, about 100 nM or less, about 50 nM or less, about 25 nM or less, about 10 nM or less, about 5 nM or less, or about 1 nM or less.

In certain embodiments, the compounds of Formula (I) are a selective inhibitors of cancer stem-like cells (CSC). In another embodiment, the compounds of Formula (I) possess anti-tumor effects and inhibit the growth of CSC in NSCLC cells.

In certain embodiments, the present disclosure feature compounds of Formula (I) that reverse CSC-associated gene expression.

In one embodiment, the compounds of Formula (I) overcome lung cancer drug resistance. In another embodiment, the compounds of Formula (I) overcome NSCLC drug resistance. In yet another embodiment, the NSCLC cells express epidermal growth factor receptor-tyrosine kinase inhibitor (EGFR-TKI) resistance.

In certain embodiments, the present disclosure features one or more compounds of Formula (I) in combination with other anti-cancer agents, e.g., cisplatin or gefitinib, that provide synergistic cytotoxic effects on resistant lung cancer cells, e.g., H441GL, A549 or H1299.

Also provided herein are pharmaceutical compositions comprising one or more pharmaceutically acceptable carriers and one or more compounds of Formula (I) described herein.

In one embodiment, the compound of Formula (I) is isotopically labeled.

For example, deuterium labeled compounds can be prepared using any of a variety of art-recognized techniques. For example, deuterium labeled compounds of Formula (I) described herein or the compounds listed herein can generally be prepared by carrying out the procedures described herein, by substituting a readily available deuterium labeled reagent for a non-deuterium labeled reagent.

In another aspect, the present disclosure features a method of treating cancer (e.g., a lung cancer, such as non-small cell lung cancer or NSCLC, a colon cancer, a breast cancer, or a pancreatic cancer), the method comprising administering to a subject in need thereof a therapeutically effective amount of a compound of Formula (I):

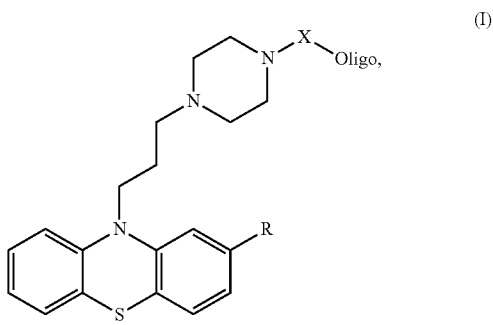

(I)

or a pharmaceutically acceptable salt thereof, wherein:

Oligo is an oligomer or a co-oligomer selected from the group consisting of —[CH$_2$CH(OR$^1$)CH$_2$O]$_m$—R$^2$, —[CH$_2$CH$_2$O]$_n$—R$^3$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$;

R is H, halo, C$_1$-C$_4$ alkyl substituted with one or more halo, or —S—C$_1$-C$_4$ alkyl;

each of R$^1$, R$^2$ and R$^3$ independently is H or C$_1$-C$_4$ alkyl;

X is a bond, C(O), C(O)O, or C(O)CH$_2$O;

m is an integer ranging from 2 to 16, and n is an integer ranging from 3 to 16.

In one embodiment, the lung cancer is NSCLC. In certain embodiments, the NSCLC is adenocarcinoma, squamous cell carcinoma or large cell carcinoma.

In one embodiment, the cancer is a colon cancer, a breast cancer, or a pancreatic cancer.

In one embodiment, the subject is human or non-human animals.

Unless otherwise stated, any description of a method of treatment includes use of one or more compounds of Formula (I), or in combination with other anti-cancer agents, e.g., cisplatin or gefitinib, to provide such treatment as described herein, as well as use of one or more compounds of Formula (I), or in combination with other anti-cancer agents, e.g., cisplatin or gefitinib, to prepare or manufacture a medicament to treat or prevent such condition. The treatment includes treatment of human or non-human animals including rodents and other disease models. Methods described herein may be used to identify suitable candidates for treating or preventing cancer via inhibition of CSCs. For example, the disclosure also provides methods of identifying an inhibitor of CSC.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the disclosure. In the case of conflict, the present disclosure, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

In addition to anti-histaminic, anti-emetic, sedative and anti-cholinergic effects, certain phenothiazine compounds such as prochlorperazine (PCP) and trifluoperazine (TFP) have shown to possess anti-tumor effects by inhibiting the growth of CSCs in human NSCLC cell lines (see, e.g., US 2014/0294994, WO2013/060305 and WO2015/184794). PCP has shown cytotoxicity to NSCLC cells (see, e.g., WO2015/184794). Similarly, TFP and N-desmethyl prochlorperazine (10-[3-(1-Piperazinyl)propyl]-2-chloro-10H-phenothiazine (NDP)) have also shown cytotoxicity to NSCLC cells (see, e.g., Yeh et al., *Am. J. Respir. Crit. Care Med.* 186, 1180 (2012), WO2013/060305 and WO2015/184794). The structures of PCP, TFP, NDP, and N-desmethyl trifluoperazine (NDT) are provided in the table below.

| Compound | Structure |
|---|---|
| PCP | 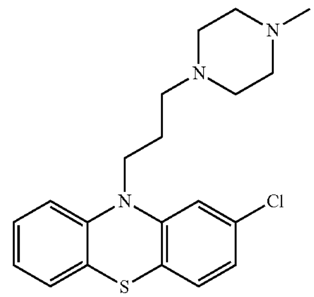 |
| NDP | 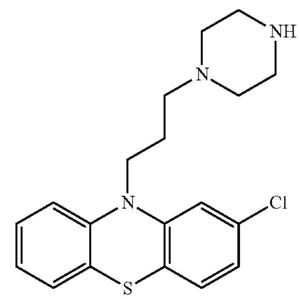 [SMILES: Clc1ccc2c(c1)N(CCCN1CCNCC1)c1ccccc1S2] |
| TFP | 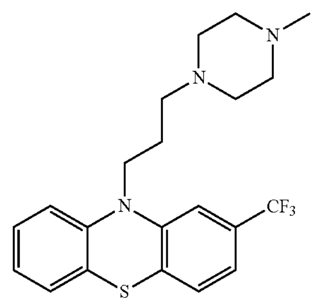 [SMILES: CN1CCN(CCCN2c3ccccc3Sc3ccc(C(F)(F)F)cc32)CC1] |
| NDT | 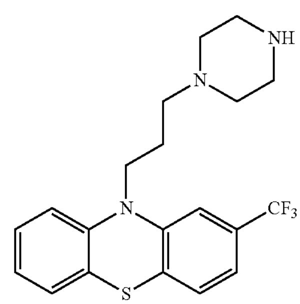 [SMILES: FC(F)(F)c1ccc2c(c1)N(CCCN1CCNCC1)c1ccccc1S2] |

Conjugates of promethazine were synthesized by N-alkylation of N-desmethyl promethazine with methoxypolyethyleneglycols (mPEGs) (see, e.g., US 2012/0046279), and were shown to display high affinity binding to the H$_1$ receptor. However, polyethyleneglycol (PEG) conjugation resulted in reducing binding affinity of promethazine. Moreover, as the size of mPEGs increased, the binding affinity decreased. mPEG conjugates of N-desmethyl phenothiazine via an amide linkage have also been reported (see, e.g., Roberts et al., *Adv. Drug Delivery Rev.* 2002, 54, 459 and US 2005/0080075).

The present disclosure provides novel oligomer-phenothiazine conjugates which circumvent the problems encountered with chemotherapy drug resistance. Advantages of the oligomer-phenothiazine conjugates disclosed herein include increased cytotoxicity to drug-resistant cancer cells, thus, leading to improved methods for cancer therapy.

The present disclosure also provides synthetic methods for making the compounds disclosed herein, pharmaceutical compositions containing these compounds, and various uses of the compounds.

In one aspect, the present disclosure provides compounds of Formula (I):

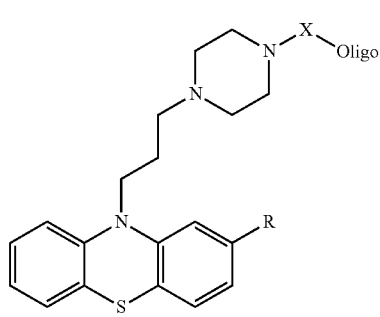

(I)

or a pharmaceutically acceptable salt thereof, wherein:

Oligo is an oligomer or a co-oligomer selected from the group consisting of —[CH$_2$CH(OR$^1$)CH$_2$O]$_m$—R$^2$, —[CH$_2$CH$_2$O]$_n$—R$^3$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$;

R is H, halo, $C_1$-$C_4$ alkyl substituted with one or more halo, or —S—$C_1$-$C_4$ alkyl;

each of R$^1$, R$^2$ and R$^3$ independently is H or $C_1$-$C_4$ alkyl;

X is a bond, C(O), C(O)O, or C(O)CH$_2$O;

m is an integer ranging from 2 to 16, and n is an integer ranging from 3 to 16, and when Oligo is —[CH$_2$CH$_2$O]$_n$—R$^3$, in which n is 12 or 13 and R$^3$ is methyl, then X is C(O), C(O)O, or C(O)CH$_2$O.

The compounds of Formula (I) can have one or more of the following features when applicable:

For example, R is halo or $C_1$-$C_4$ alkyl substituted with one or more F.

For example, R is Cl, CF$_3$, SCH$_3$, or H.

For example, R is Cl.

For example, R is CF$_3$.

For example, R is SCH$_3$.

For example, X is a bond.

For example, X is C(O)O.

For example, X is C(O)CH$_2$O.

For example, X is C(O).

For example, Oligo is an oligomer selected from —[CH$_2$CH(OR$^1$)CH$_2$O]$_m$—R$^2$ and —[CH$_2$CH$_2$O]$_n$—R$^3$.

For example, Oligo is a co-oligomer selected from —[CH$_2$CH(OR$^1$)CH$_2$O]$_m$—[CH$_2$CH$_2$O]$_n$—R$^2$ and —[CH$_2$CH$_2$O]$_n$—[CH$_2$CH(OR$^1$)CH$_2$O]$_m$—R$^2$.

For example, n is 3, 6, 9, 12 or 16.

For example, n is ranging from 3 to 11, e.g., n is 3, 4, 5, 6, 7, 8, 9, 10, or 11.

For example, n is ranging from 3 to 9, e.g., n is 3, 4, 5, 6, 7, 8, or 9.

For example, n is ranging from 14 to 16, e.g., n is 14, 15, or 16.

For example, n is 3, 6, or 9.

For example, m is ranging from 2 to 9, e.g., m is 2, 3, 4, 5, 6, 7, 8, or 9.

For example, m is ranging from 2 to 6, e.g., m is 2, 3, 4, 5, or 6.

For example, m is ranging from 6 to 12, e.g., m is 6, 7, 8, 9, 10, 11, or 12.

For example, m is ranging from 12 to 16, e.g., m is 12, 13, 14, 15, or 16.

For example, m is 3, 6, or 9.

For example, m is 3.

For example, m is 3 and n is ranging from 3 to 9 (e.g., n is 3, 6, or 9).

For example, when Oligo is a co-oligomer, the sum of m and n is not greater than 16, not greater than 12, or not greater than 9. For example, the sum of m and n is ranging between 5 and 16 (e.g., the sum is 5, 6, 7, 8, 9, 10, 11, 12, 13, 14, 15, or 16).

For example, each R$^1$ independently is H or methyl.

For example, each R$^1$ is H.

For example, each R$^1$ is methyl.

For example, R$^2$ is H or methyl.

For example, R$^2$ is H.

For example, R$^2$ is methyl.

For example, R$^3$ is H.

For example, R$^3$ is methyl.

In another aspect, the present disclosure provides a pharmaceutical composition comprising a compound of Formula (I) and a pharmaceutically acceptable carrier.

In yet another aspect, the present disclosure provides a method of treating cancer comprising administering to a subject in need thereof a therapeutically effective amount of a compound of Formula (I).

In addition, the present disclosure also provides a method of treating cancer comprising administering to a subject in need thereof a therapeutically effective amount of a compound of Formula (I):

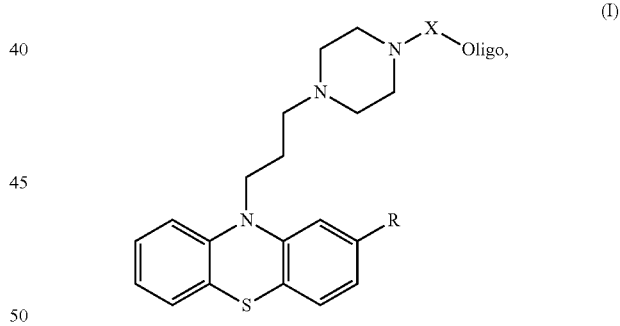

(I)

or a pharmaceutically acceptable salt thereof, wherein:

Oligo is an oligomer or a co-oligomer selected from the group consisting of —[CH$_2$CH(OR$^1$)CH$_2$O]$_m$—R$^2$, —[CH$_2$CH$_2$O]$_n$—R$^3$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$;

R is H, halo, $C_1$-$C_4$ alkyl substituted with one or more halo, or —S—$C_1$-$C_4$ alkyl;

each of R$^1$, R$^2$ and R$^3$ independently is H or $C_1$-$C_4$ alkyl;

X is a bond, C(O), C(O)O, or C(O)CH$_2$O;

m is an integer ranging from 2 to 16, and n is an integer ranging from 3 to 16.

The methods disclosed herein can have one or more of the following features when applicable:

For example, the cancer is a lung cancer.

For example, the cancer is non-small cell lung cancer.

For example, the non-small cell lung cancer is adenocarcinoma, squamous cell carcinoma or large cell carcinoma.

For example, the cancer is a colon cancer,

For example, the cancer is a breast cancer,

For example, the cancer is a pancreatic cancer

For example, the subject is a human.

For example, the method further comprises administering to the subject an anti-cancer agent.

For example, the anti-cancer agent is cisplatin or gefitinib.

For example, the compound of Formula (I) is cytotoxic to NSCLC cells. For example, the compound of Formula (I) is an inhibitor of NSCLC cells, such as H441GL (ATCC® HTB-174™), A549 (ATCC® CCL-185™) or H1299 (ATCC® CCL-5803™), with a cellular inhibition $IC_{50}$ value of about 15 μM or less, about 10 μM or less, about 5 μM or less, about 1 μM or less, about 500 nM or less, about 300 nM or less, about 200 nM or less, about 100 nM or less, about 50 nM or less, about 25 nM or less, about 10 nM or less, about 5 nM or less, or about 1 nM or less.

In another aspect, the present disclosure features a method of treating cancer, e.g., lung cancer (such as NSCLC), the method comprising administering to a subject in need thereof a therapeutically effective amount of a compound of Formula (I).

For example, the compound of Formula (I) inhibits NSCLC cells, e.g., H441GL, A549 or H1299 cells. For example, the NSCLC cells express EGFR-TKI resistance. For example, the non-small cell lung cancer (NSCLC) cells express cancer stem-like cell (CSC) associated gene expression.

In one embodiment, a compound of Formula (I) is used in combination with other anti-cancer agents, e.g., cisplatin or gefitinib.

For example, the compound of Formula (I) is cytotoxic to cancer cells. For example, the compound of Formula (I) is an inhibitor of colon cancer cells, such as HCT116 (ATCC® CCL-247™) or DLD1 (ATCC® CCL-221™), breast cancer cells, such as MCF7 (ATCC® HTB-22™) or MDA-MB-231(ATCC® HTB-26™), and pancreatic cancer cells, such as PANC-1 (ATCC® CRL-1469™) or SUIT-2, with a cellular inhibition $IC_{50}$ value of about 15 μM or less, about 10 μM or less, about 5 μM or less, about 1 μM or less, about 500 nM or less, about 300 nM or less, about 200 nM or less, about 100 nM or less, about 50 nM or less, about 25 nM or less, about 10 nM or less, about 5 nM or less, or about 1 nM or less.

Without wishing to be bound by any theory, it is believed that the contemplated compounds of Formula (I) disclosed herein, may treat cancer (e.g., NSCLC, colon cancer, breast cancer or pancreatic cancer) by selectively inhibiting CSCs.

In yet another aspect, the present disclosure features a method of preparing a compound of Formula (I).

The present disclosure also features a pharmaceutical composition comprising a compound of Formula (I) or a pharmaceutically acceptable salt thereof, and a pharmaceutically acceptable carrier.

Representative compounds of the present disclosure include compounds listed in Table 1 or salts thereof.

TABLE 1

| Compound No. | Structure |
|---|---|
| 5-1a | 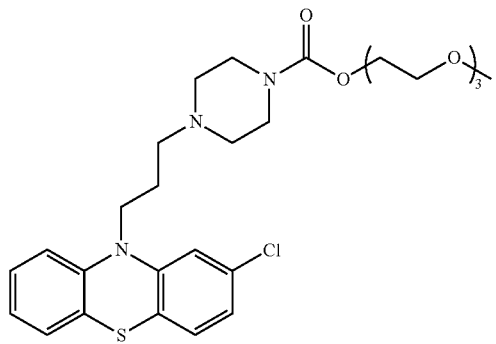 |
| 5-2a | 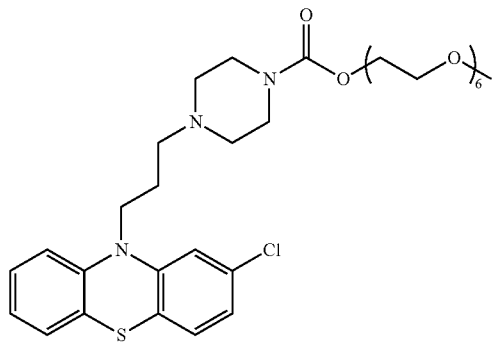 |

TABLE 1-continued
| Compound No. | Structure |
|---|---|
| 5-3a | 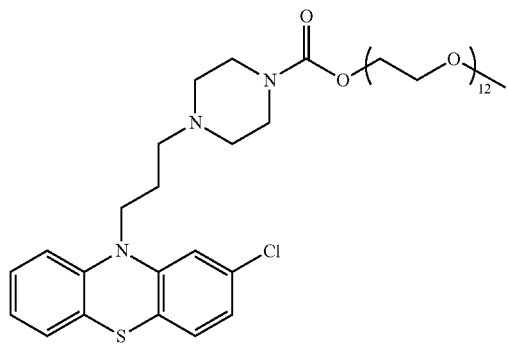 |
| 5-4a | 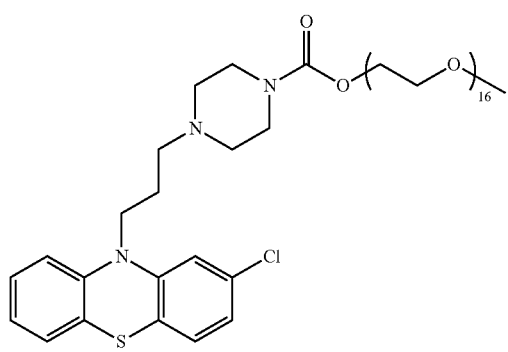 |
| 5-1b | 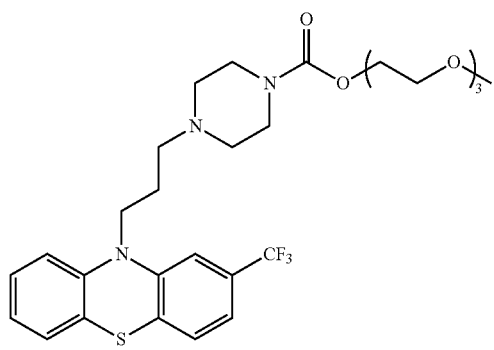 |
| 5-2b | 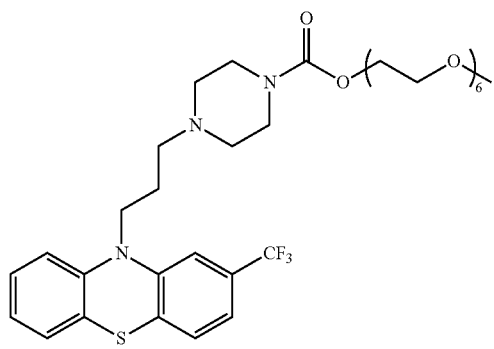 |

TABLE 1-continued
| Compound No. | Structure |
|---|---|
| 5-3b | 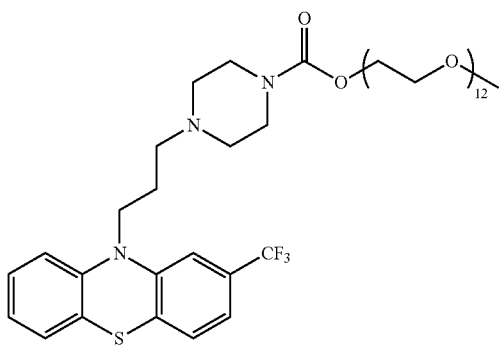 |
| 5-4b | 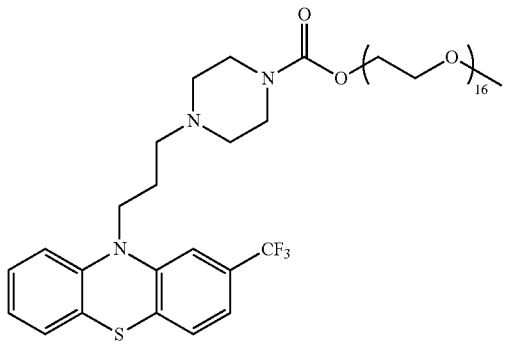 |
| 4-1a | 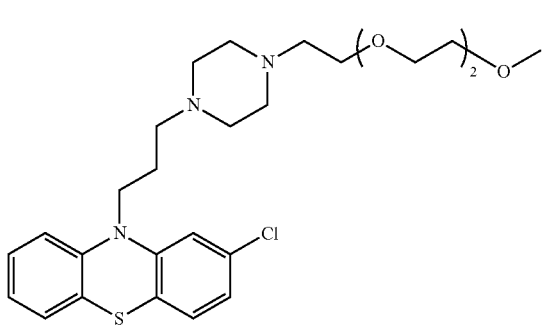 |
| 4-2a | 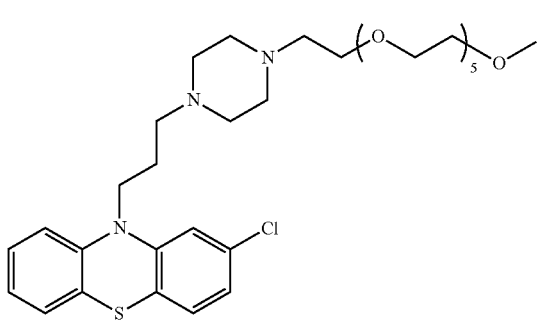 |

TABLE 1-continued

| Compound No. | Structure |
|---|---|
| 4-3a | Phenothiazine with 2-Cl, N-propyl-piperazine-N'-(CH₂CH₂O)₁₁-CH₃ |
| 4-4a | Phenothiazine with 2-Cl, N-propyl-piperazine-N'-(CH₂CH₂O)₁₅-CH₃ |
| 4-1b | Phenothiazine with 2-CF₃, N-propyl-piperazine-N'-(CH₂CH₂O)₂-CH₃ |
| 4-2b | Phenothiazine with 2-CF₃, N-propyl-piperazine-N'-(CH₂CH₂O)₅-CH₃ |
| 4-3b | Phenothiazine with 2-CF₃, N-propyl-piperazine-N'-(CH₂CH₂O)₁₁-CH₃ |

TABLE 1-continued
| Compound No. | Structure |
|---|---|
| 4-4b | 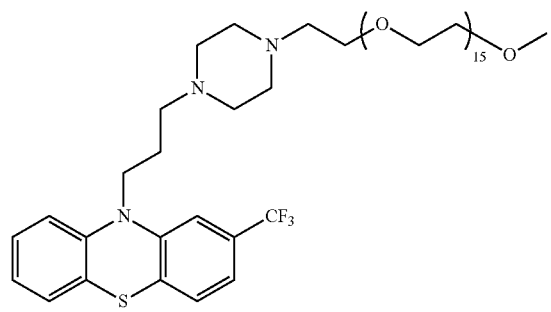 |
| 6-1a | 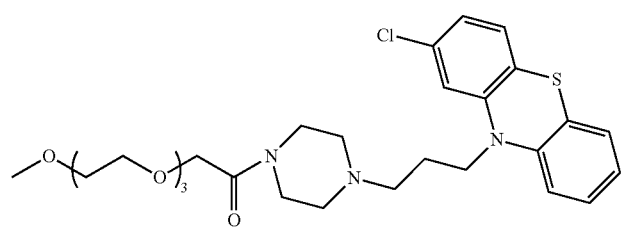 |
| 6-2a | 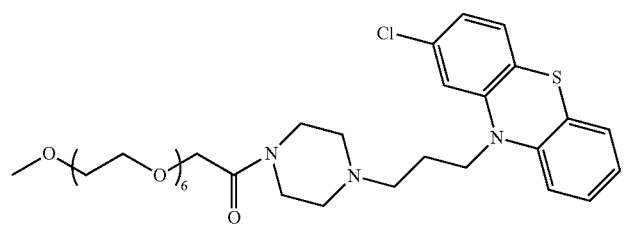 |
| 6-3a | 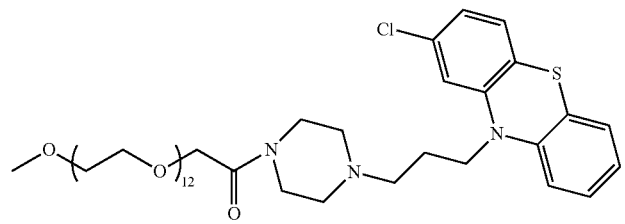 |
| 6-4a | 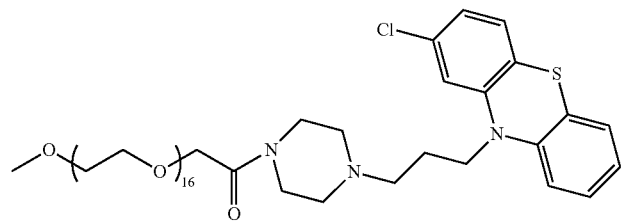 |
| 6-1b | 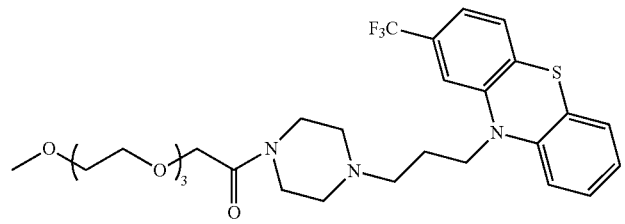 |

TABLE 1-continued

| Compound No. | Structure |
|---|---|
| 6-2b | 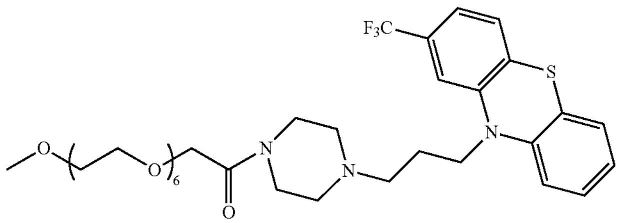 |
| 6-3b | 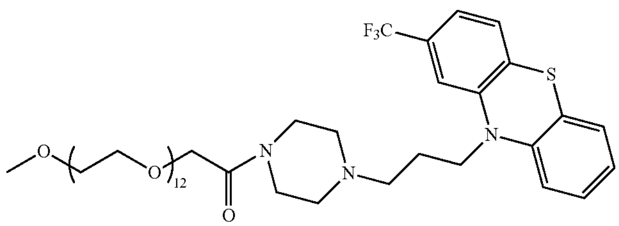 |
| 6-4b | 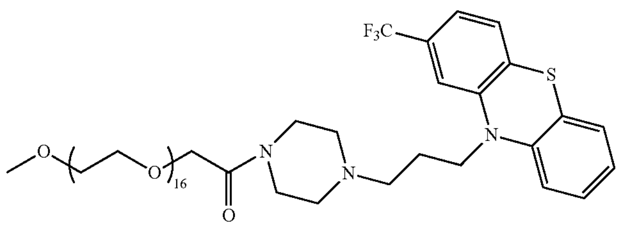 |
| 24a | 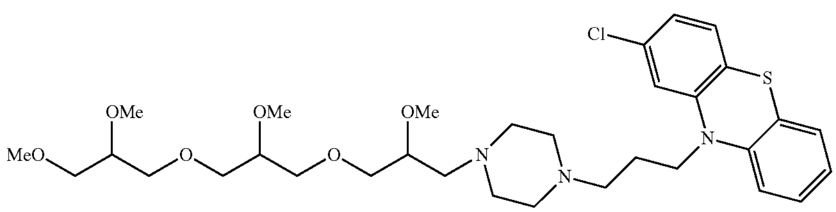 [SMILES: COCC(COCC(COCC(CN1CCN(CCCN2c3ccccc3Sc3ccc(Cl)cc32)CC1)OC)OC)OC] |
| 24b | 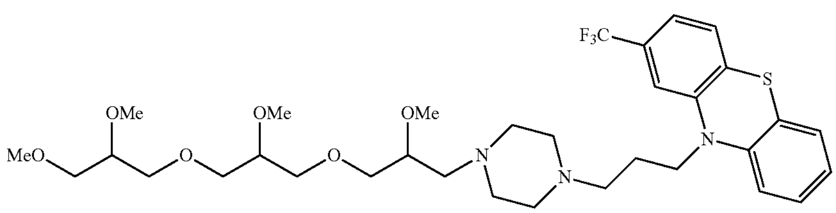 [SMILES: COCC(COCC(COCC(CN1CCN(CCCN2c3ccccc3Sc3ccc(C(F)(F)F)cc32)CC1)OC)OC)OC] |
| 25-1a | 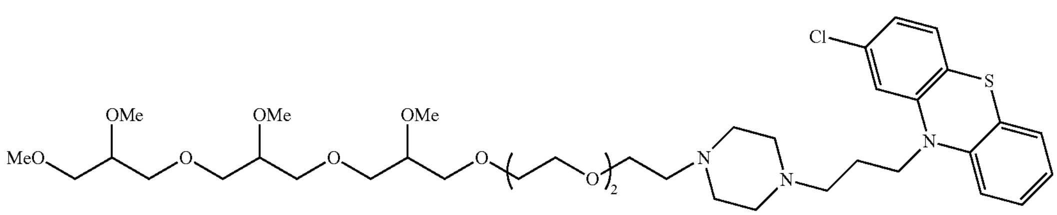 |
| 25-1b | 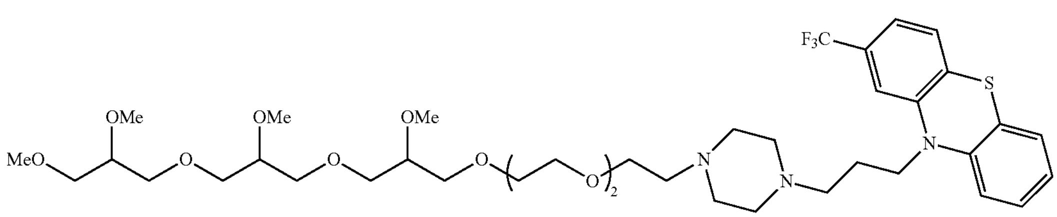 |

TABLE 1-continued
| Compound No. | Structure |
|---|---|
| 25-2a | 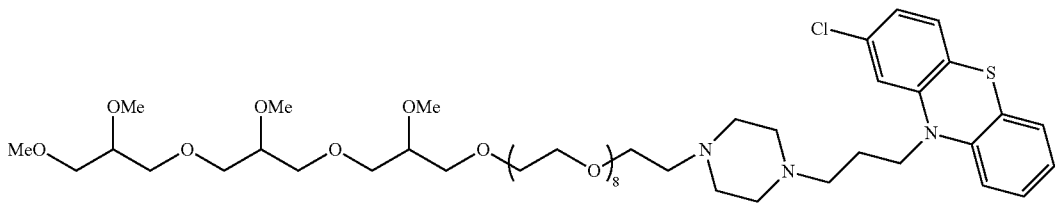 |
| 25-2b | 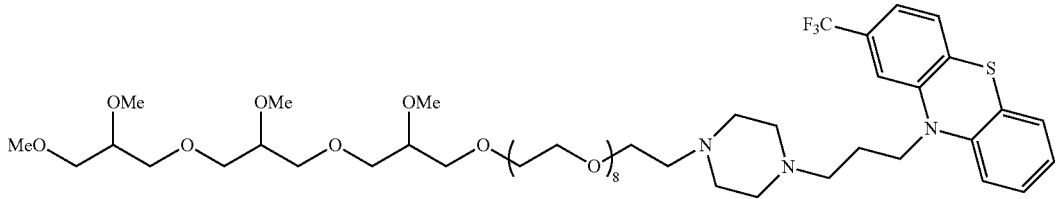 |
| 26-1a | 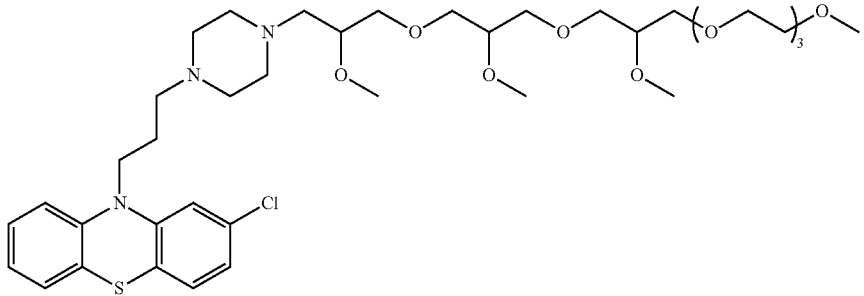 |
| 26-1b | 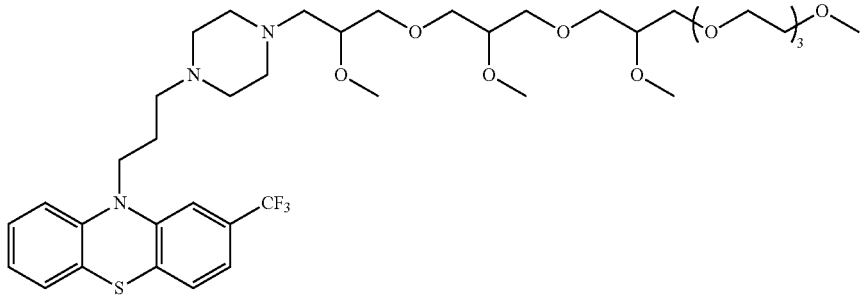 |
| 26-2a | 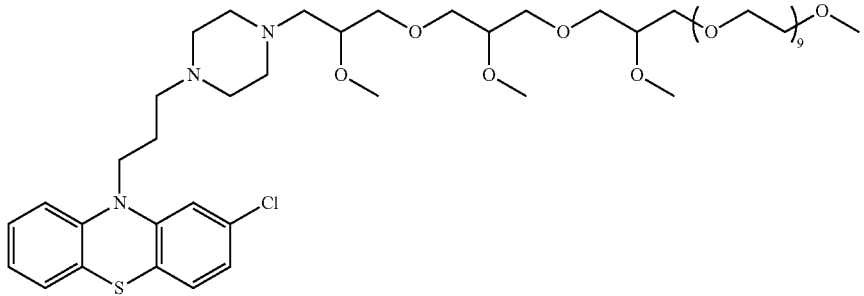 |

TABLE 1-continued

| Compound No. | Structure |
|---|---|
| 26-2b | 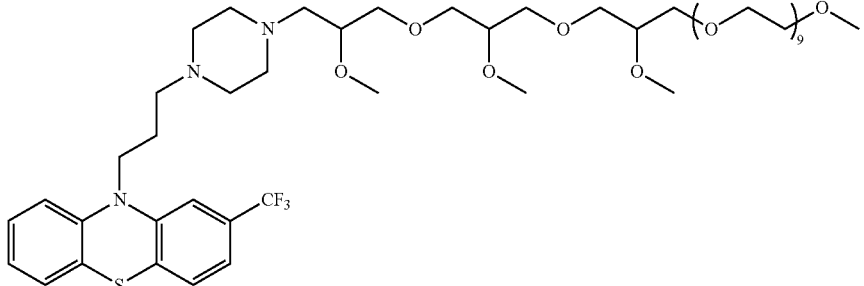 |
| 33a | 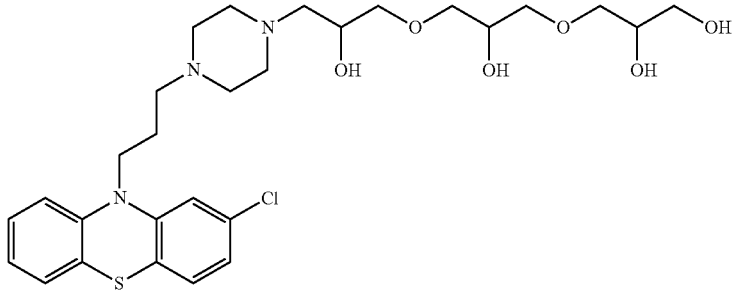 [SMILES: OCC(O)COCC(O)COCC(O)CN1CCN(CCCN2c3ccccc3Sc3ccc(Cl)cc32)CC1] |
| 33b | 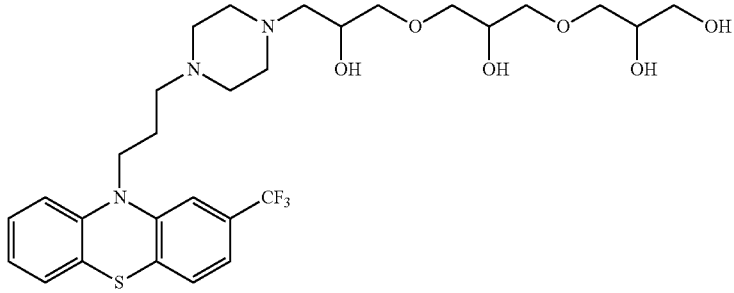 |

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The term "and/or" is used in this disclosure to mean either "and" or "or" unless indicated otherwise.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ or $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. "Stable compound" and "stable structure" are meant to indicate a compound that is sufficiently robust to survive isolation to a useful degree of purity from a reaction mixture, and formulation into an efficacious therapeutic agent.

When any variable (e.g., R, $R^1$, $R^2$ or $R^3$) occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms.

The compounds of the present disclosure include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In certain embodiments, "combination therapy" is intended to embrace administration of two or more therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the disclosure "combination therapy" also embraces the administration of the therapeutic agents as described above in further combination with other biologically active ingredients and non-drug therapies (e.g., surgery or radiation treatment).

In certain aspects of the disclosure, the combination therapies featured in the present disclosure can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

Combination therapy can be achieved by administering two or more agents, e.g., one or more compounds of Formula (I) and one or more other therapeutic agents, each of which is formulated and administered separately, or by administering two or more agents in a single formulation.

Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The present disclosure also provides pharmaceutical compositions comprising a compound of the disclosure or pharmaceutically acceptable salts thereof, and one or more other therapeutic agents disclosed herein, mixed with pharmaceutically suitable carriers or excipient(s) at doses to treat or prevent a cancer (e.g., a lung cancer, a colon cancer, breast cancer or pancreatic cancer) as described herein. In one aspect, the present invention also provides pharmaceutical compositions comprising any compound of the present disclosure or pharmaceutically acceptable salts thereof, and one or more other therapeutic agents, mixed with pharmaceutically suitable carriers or excipient (s) at doses to treat or prevent lung cancer as described herein. The pharmaceutical compositions of the present invention can also be administered in combination with other therapeutic agents or therapeutic modalities simultaneously, sequentially, or in alternation. In some embodiments, a pharmaceutical composition of a compound of Formula (I) is administered in combination with another anti-cancer agents, e.g., cisplatin or gefitinib.

A "pharmaceutical composition" is a formulation containing the compound of the present disclosure in a form suitable for administration to a subject. A compound of the present disclosure and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound of the present disclosure and one or more other therapeutic agents described herein can be formulated as one pharmaceutical composition.

In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier" means an excipient that is useful in preparing a pharmaceutical composition that is generally safe, non-toxic and neither biologically nor otherwise undesirable, and includes excipient that is acceptable for veterinary use as well as human pharmaceutical use.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the present disclosure can be administered to a subject in many of the well-known methods currently used for chemotherapeutic treatment. For example, for treatment of cancers, a compound of the present disclosure may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound of Formula (I), the therapeutically effective amount can be estimated initially either in cell culture assays, e.g., CSCs, or in animal models, usually rats, mice, rabbits, dogs, pigs, or monkeys. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In therapeutic applications, the dosage of the compounds of Formula (I) described herein, other therapeutic agents described herein, compositions comprising a compound of the disclosure and one or more other therapeutic agents, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.017 mg/kg per day to about 10 mg/kg per day. In preferred aspects, dosages can range from about 0.067 mg/kg per day to about 5 mg/kg per day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present disclosure are capable of further forming salts. All of these forms are also contemplated within the scope of the claimed disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

It should be understood that all references to pharmaceutically acceptable salts include solvent addition forms (solvates) or crystal forms (polymorphs) as defined herein, of the same salt.

The compounds of the present disclosure can also be prepared as esters, for example, pharmaceutically acceptable esters. For example, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

Techniques for formulation and administration of the disclosed compounds of the disclosure can be found in *Remington: the Science and Practice of Pharmacy,* $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

As used herein, a "subject in need thereof" is a subject having lung cancer, or a subject having an increased risk of developing such disorder relative to the population at large. A subject in need thereof can have a precancerous condition. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the present disclosure includes any human subject who has been diagnosed with, has symptoms of, or is at risk of developing lung cancer. The subject of the present invention includes any human subject expressing chemotherapy resistance, e.g., epidermal growth factor receptor-tyrosine kinase inhibitor (EGFR-TKI) resistance.

A subject in need thereof may have refractory or resistant cancer (i.e., cancer that doesn't respond or hasn't yet responded to treatment). The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

As used herein, "treating" or "treat" describes the management and care of a patient for the purpose of combating a disease, condition, or disorder and includes the administration of a compound of the present disclosure, or a pharmaceutically acceptable salt or solvate thereof, to alleviate the symptoms or complications of a disease, condition or disorder, or to eliminate the disease, condition or disorder. The term "treat" can also include treatment of a cell in vitro or an animal model.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body, e.g., lung cancer spreading to nearby organs or structures.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present disclosure, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means.

An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means to those skilled in the art.

The present disclosure also provides methods for the synthesis of the compounds of Formula (I) described herein. The present disclosure also provides detailed methods for the synthesis of various disclosed compounds of the present disclosure according to the following schemes as well as those shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; Greene, T. W., Wuts, P. G. M., *Protective Groups in Organic Synthesis*, $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

Compounds of the present disclosure can be conveniently prepared by a variety of methods familiar to those skilled in the art. The compounds of Formula (I) described herein may be prepared according to the procedures illustrated in Schemes 1-7 below, from commercially available starting materials or starting materials which can be prepared using literature procedures. The variables (e.g., R and n, etc.) in Schemes 1-7 are as defined in any Formula described herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, $3^{rd}$ edition, John Wiley & Sons: New York, 1999.

Preferred protecting groups include, but are not limited to:
For a hydroxyl moiety: TBDPS, benzyl, THP In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

Scheme 1 below illustrates the preparation of compounds 1-1, 1-2, 1-3, 1-4, 1-5, 2-1, 2-2, 2-3, 2-4, 3-1, 3-2, 3-3 and 3-4.

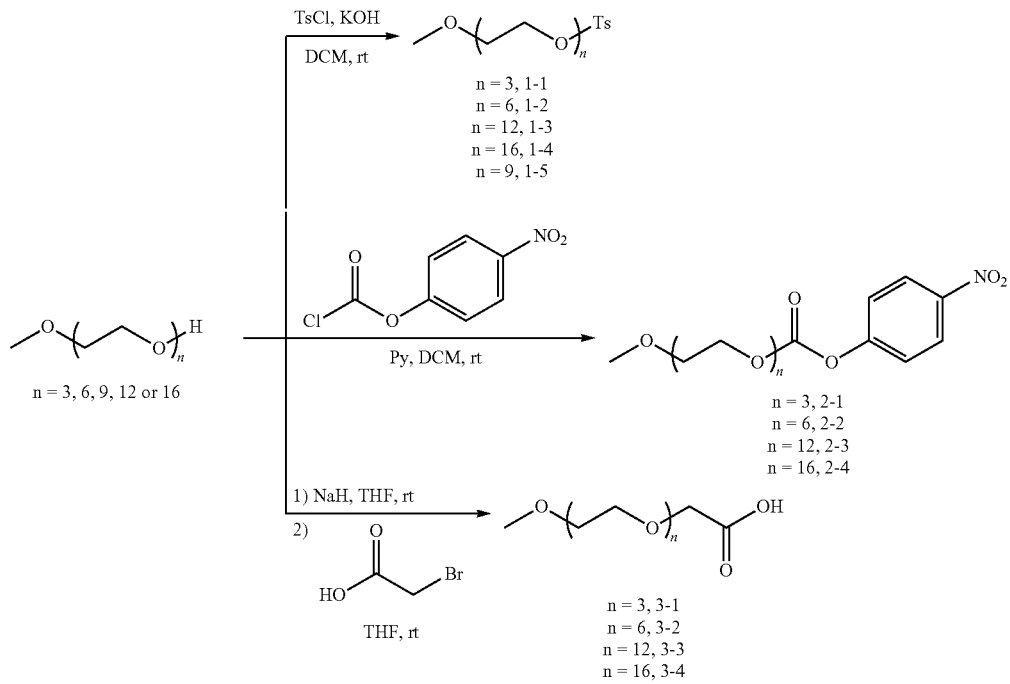

As illustrated in Scheme 1 above, to a solution of CH$_3$O—[CH$_2$CH$_2$O]$_n$—H (n=3, 6, 9, 12, or 16) in an organic solvent, e.g., (1) dichloromethane (DCM) or tetrahydrofuran (THF)/water, tosyl chloride (TsCl) and potassium hydroxide are added, (2) pyridine (Py) in anhydrous DCM, 4-nitrophenyl chloroformate is added, or (3) bromoacetic acid in THF, sodium hydride (NaH) is added, at e.g., 0° C. The reaction mixture is stirred at, e.g., room temperature. Upon separation and purification, Compound 1-1, 1-2, 1-3, 1-4, 1-5, 2-1, 2-2, 2-3, 2-4, 3-1, 3-2, 3-3 or 3-4 is afforded.

Scheme 2 below illustrates the preparation of several NDT or NDP conjugates.

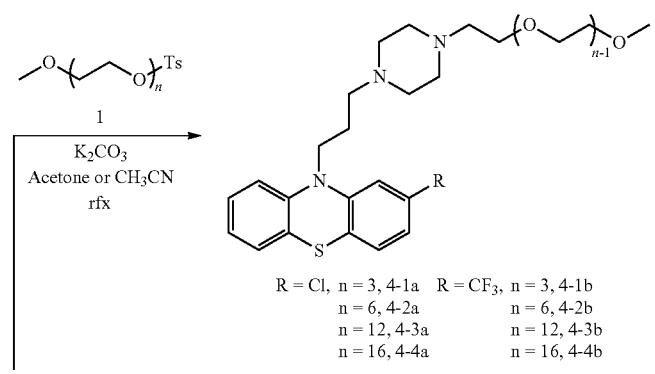

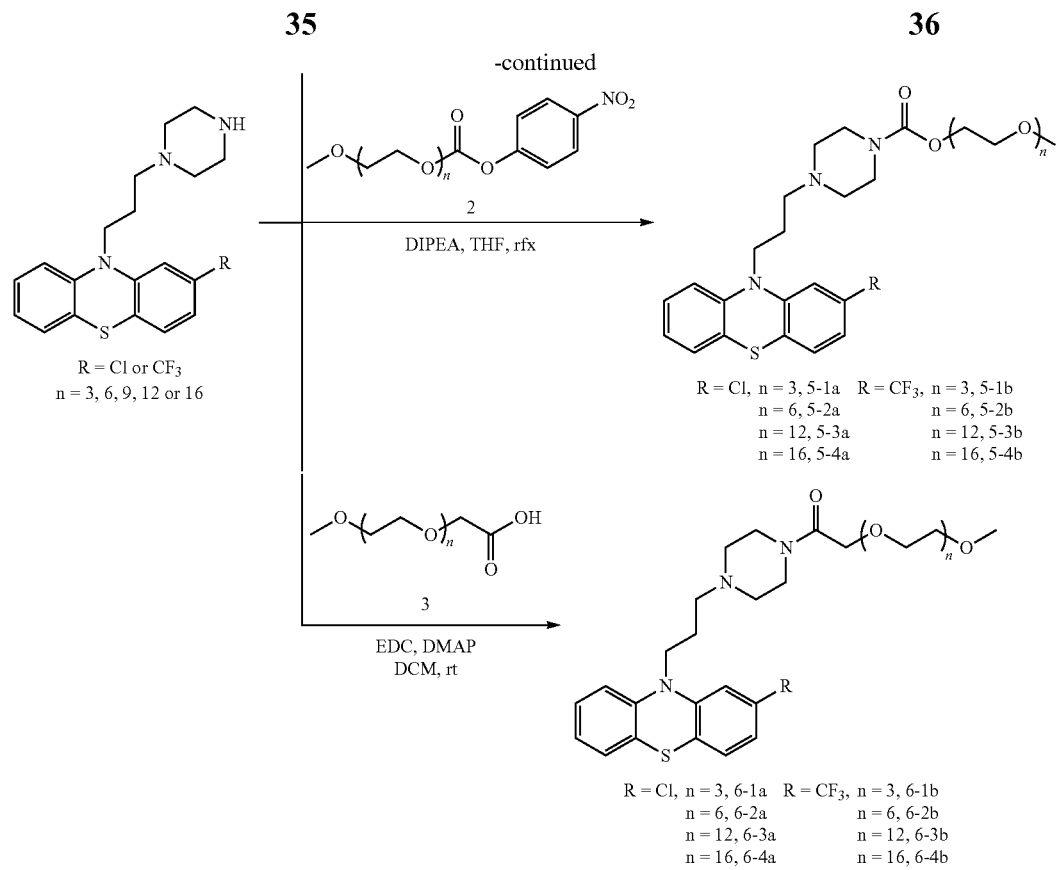

As illustrated in Scheme 2 above, (1) to a stirred solution of NDP or NDT and Ts-O—[CH$_2$CH$_2$O]$_n$—CH$_3$ (i.e., Compound 1-1 (n=3), 1-2 (n=6), 1-3 (n=12) or 1-4 (n=16)) in dry acetone or acetonitrile (CH$_3$CN), potassium carbonate (K$_2$CO$_3$) is added at, e.g., room temperature under argon, (2) to a stirred solution of NDP or NDT and 4-nitrophenyl-[CH$_2$CH$_2$O]$_n$—CH$_3$ carbonate (i.e., Compound 2-1 (n=3), 2-2 (n=6), 2-3 (n=12) or 2-4 (n=16)) in, e.g., THF, diisopropylethylamine (DIPEA) is added at, e.g., room temperature under argon, or (3) to a solution of NDP or NDT and Compound 3-1 (n=3), 3-2 (n=6), 3-3 (n=12) or 3-4 (n=16) in e.g., DCM, 1-ethyl-3-(3-dimethylaminopropyl)carbodiimide (EDC) and 4-dimethylaminopyridine (DMAP) are added at, e.g., 0° C. Upon separation from the reaction mixture and purification, Compound 4-1a, 4-2a, 4-3a, 4-4a, 4-1b, 4-2b, 4-3b, 4-4b, 5-1a, 5-2a, 5-3a, 5-4a, 5-1b, 5-2b, 5-3b, 5-4b, 6-1a, 6-2a, 6-3a, 6-4a, 6-1b, 6-2b, 6-3b or 6-4b is afforded.

Scheme 3 shows the preparation of Ts-O—[CH$_2$CH(OCH$_3$)CH$_2$O]$_m$—CH$_3$.

Scheme 3

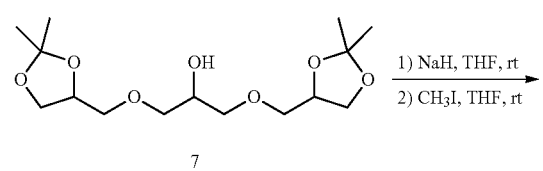

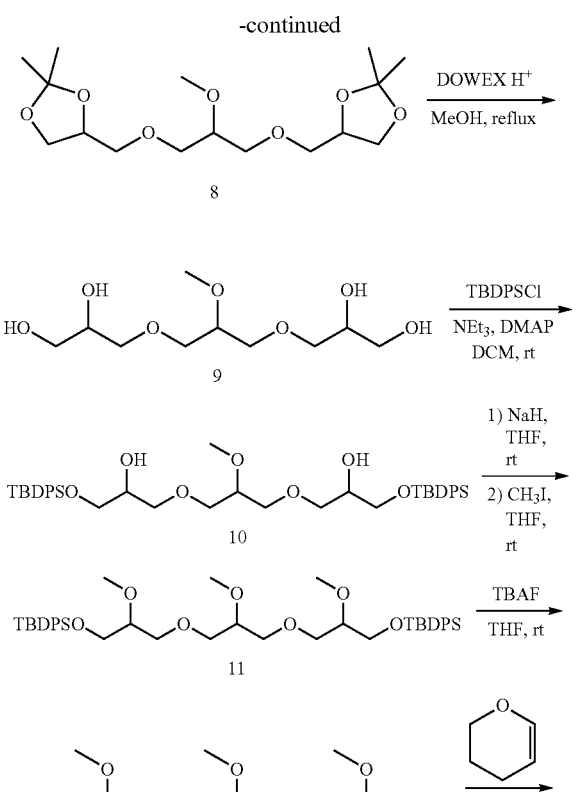

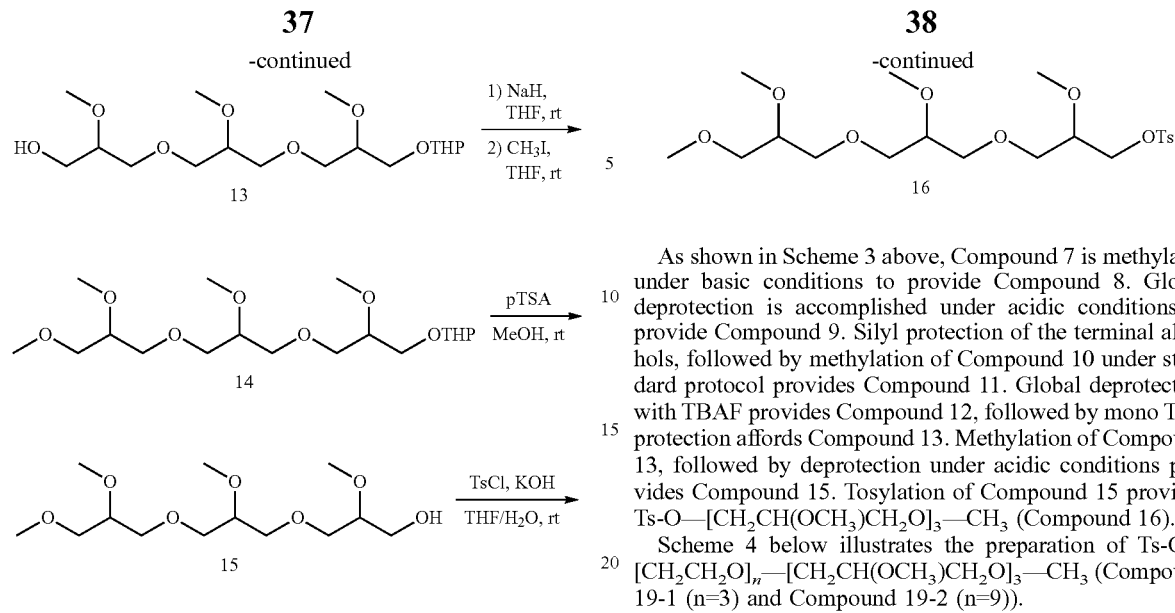

As shown in Scheme 3 above, Compound 7 is methylated under basic conditions to provide Compound 8. Global deprotection is accomplished under acidic conditions to provide Compound 9. Silyl protection of the terminal alcohols, followed by methylation of Compound 10 under standard protocol provides Compound 11. Global deprotection with TBAF provides Compound 12, followed by mono THP protection affords Compound 13. Methylation of Compound 13, followed by deprotection under acidic conditions provides Compound 15. Tosylation of Compound 15 provides Ts-O—[CH$_2$CH(OCH$_3$)CH$_2$O]$_3$—CH$_3$ (Compound 16).

Scheme 4 below illustrates the preparation of Ts-O—[CH$_2$CH$_2$O]$_n$—[CH$_2$CH(OCH$_3$)CH$_2$O]$_3$—CH$_3$ (Compound 19-1 (n=3) and Compound 19-2 (n=9)).

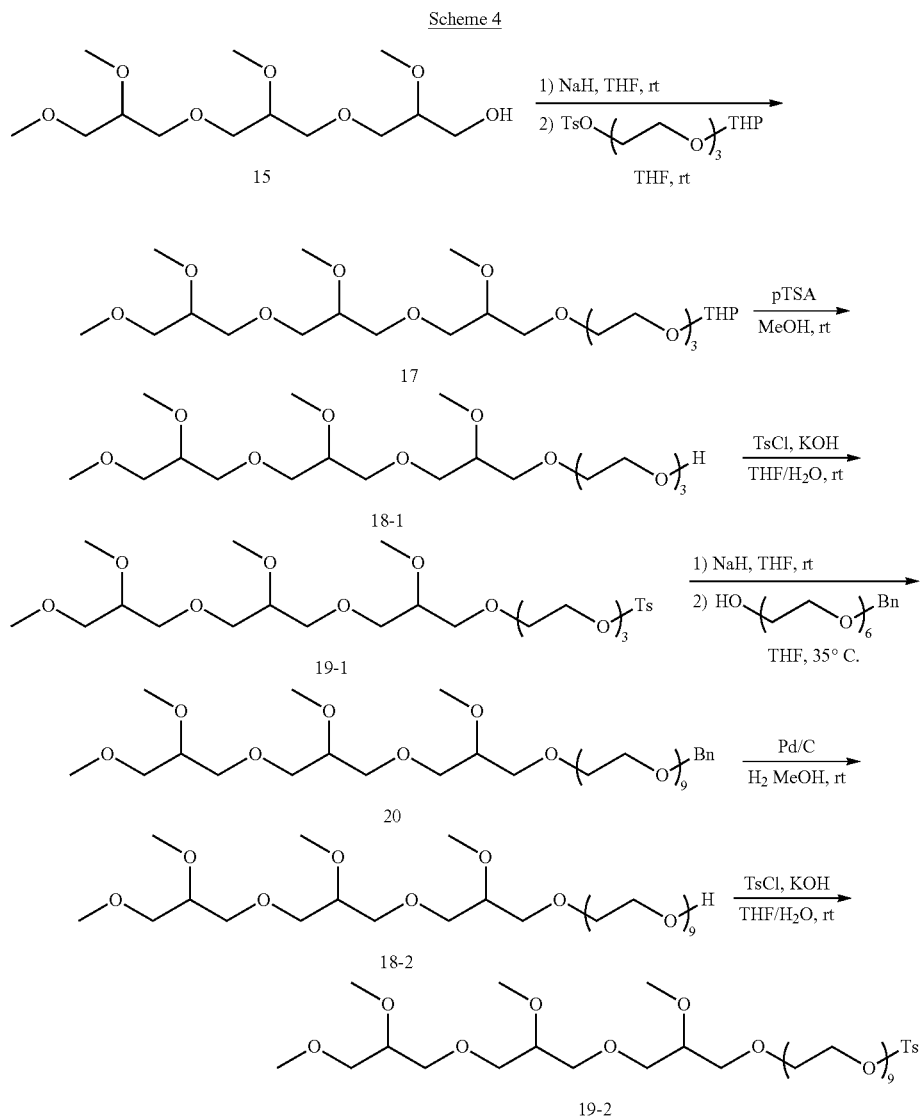

As shown in Scheme 4 above, Compound 15 is coupled under basic conditions to provide Compound 17. Deprotection is accomplished under acidic conditions to provide Compound 18-1. Tosylation of Compound 18-1 provides Compound 19-1. Coupling under basic conditions provides Compound 20. Deprotection using H2 and Pd/C provides Compound 18-2. Tosylation of Compound 18-2 provides Compound 19-2.

Scheme 5 below shows the general preparation of CH$_3$—O—[CH$_2$CH$_2$O]$_n$—[CH$_2$CH(OCH$_3$)CH$_2$O]$_3$-Ts (Compound 23-1 (n=3) and 23-2 (n=9)).

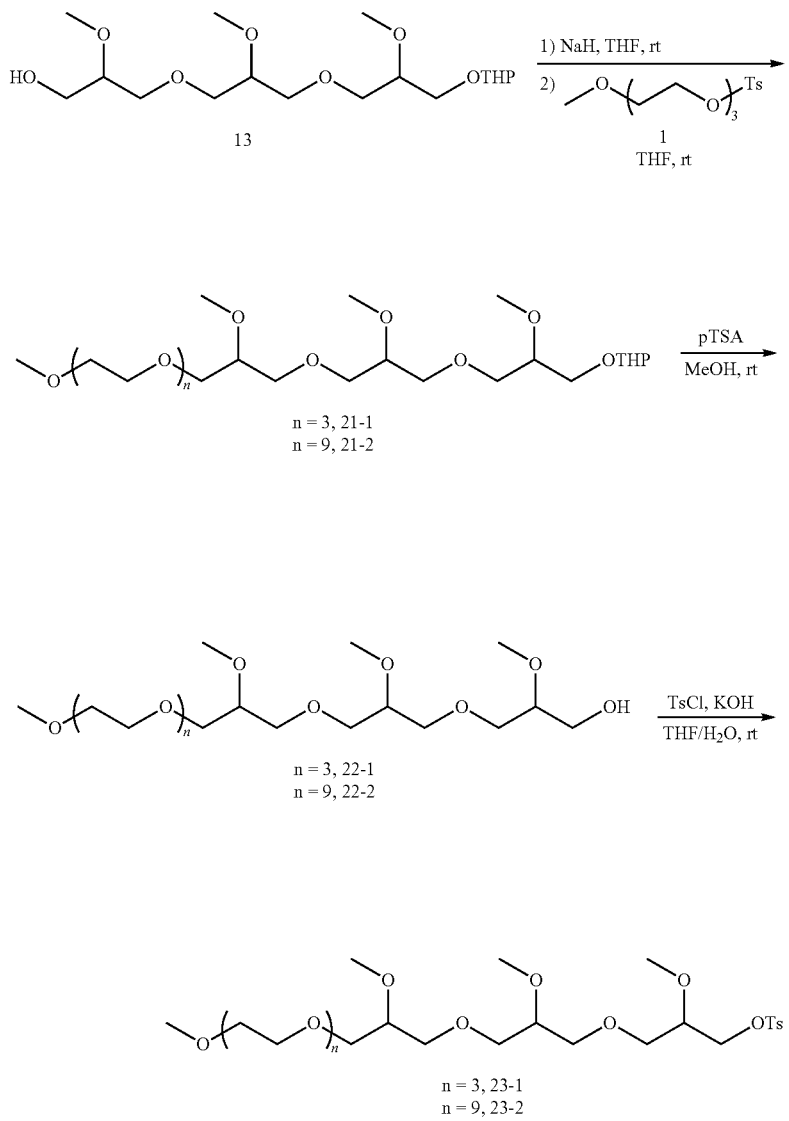

As shown in Scheme 5 above, Compound 13 is coupled under basic conditions to provide Compound 21-1 (n=3) or 21-2 (n=9). Deprotection is accomplished under acidic conditions to provide Compound 22-1 (n=3) or 22-2 (n=9). Tosylation of Compound 22-1 (n=3) or 22-2 (n=9) provides Compound 23-1 (n=3) or 23-2 (n=9) respectively.

Scheme 6 below illustrates the preparation of NDP-[CH$_2$CH(OCH$_3$)CH$_2$O]$_3$—CH$_3$, NDT-[CH$_2$CH(OCH$_3$)CH$_2$O]$_3$—CH$_3$, NDP-[CH$_2$CH$_2$O]$_n$—[CH$_2$CH(OCH$_3$)CH$_2$O]$_3$—CH$_3$, NDT-[CH$_2$CH$_2$O]$_n$—[CH$_2$CH(OCH$_3$)CH$_2$O]$_3$—CH$_3$, NDP-[CH$_2$CH(OCH$_3$)CH$_2$O]$_3$—[CH$_2$CH$_2$O]$_n$—CH$_3$ or NDT-[CH$_2$CH(OCH$_3$)CH$_2$O]$_3$—[CH$_2$CH$_2$O]$_n$—CH$_3$.

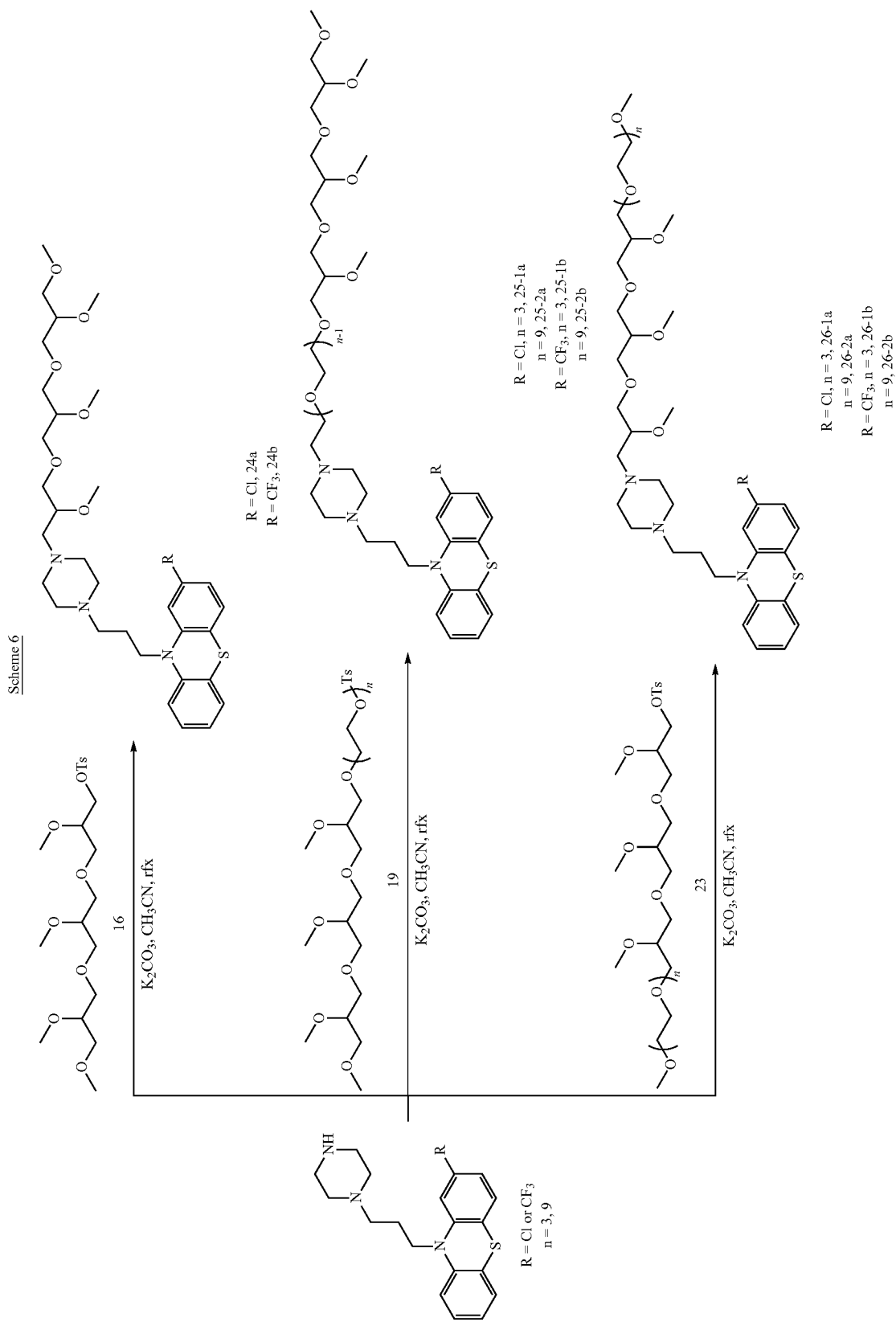

As shown in Scheme 6 above, NDP or NDT is coupled under basic conditions to provide NDP-[CH$_2$CH(OCH$_3$)CH$_2$O]$_3$—CH$_3$, NDT-[CH$_2$CH(OCH$_3$)CH$_2$O]$_3$—CH$_3$, NDP-[CH$_2$CH$_2$O]$_n$—[CH$_2$CH(OCH$_3$)CH$_2$O]$_3$—CH$_3$, NDT-[CH$_2$CH$_2$O]$_n$—[CH$_2$CH(OCH$_3$)CH$_2$O]$_3$—CH$_3$, NDP-[CH$_2$CH(OCH$_3$)CH$_2$O]$_3$—[CH$_2$CH$_2$O]$_n$—CH$_3$ or NDT-[CH$_2$CH(OCH$_3$)CH$_2$O]$_3$—[CH$_2$CH$_2$O]$_n$—CH$_3$.

Scheme 7 below illustrates the preparation of NDP-[CH$_2$CH(OH)CH$_2$O]$_3$—H and NDT-[CH$_2$CH(OH)CH$_2$O]$_3$—H.

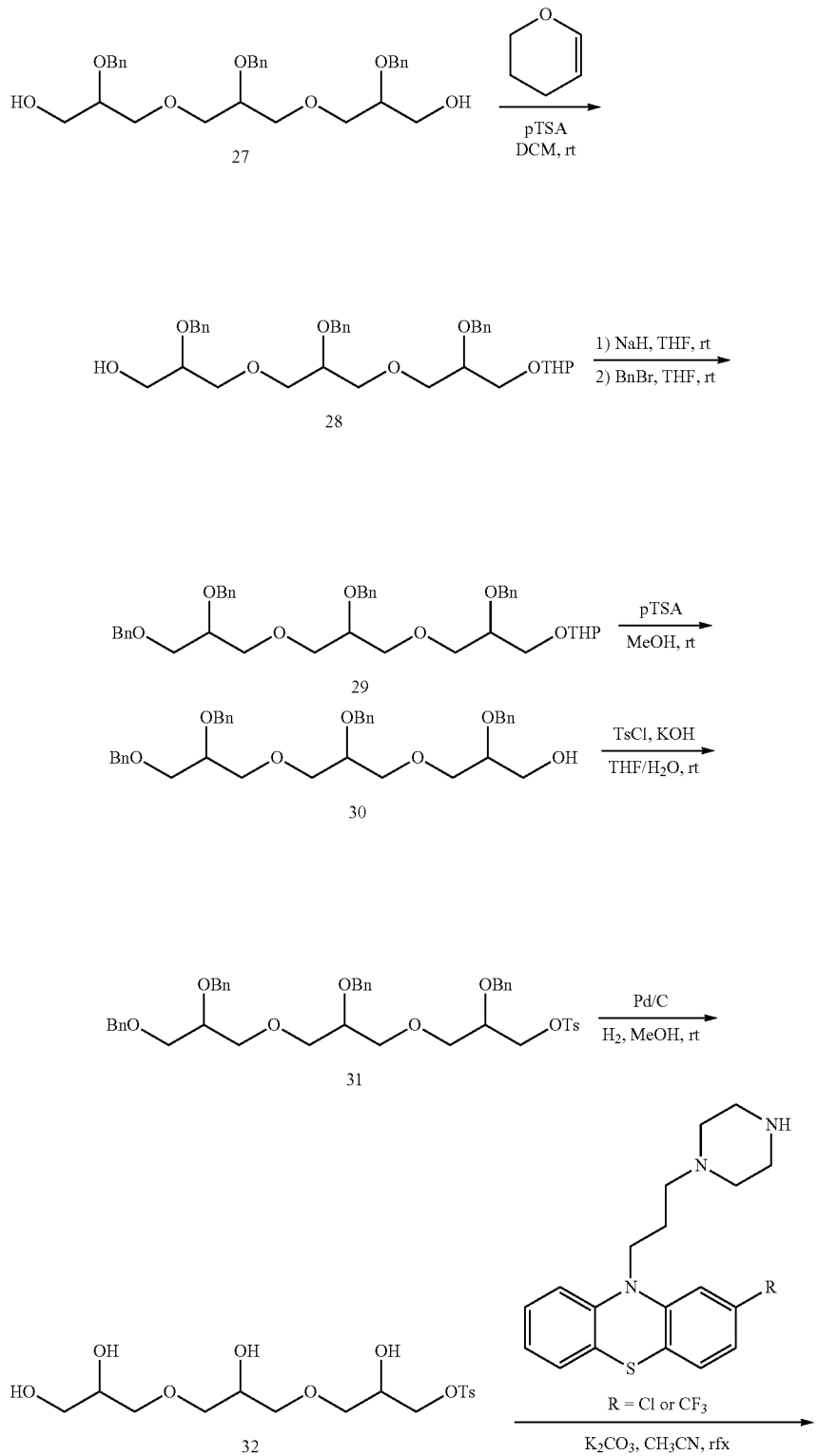

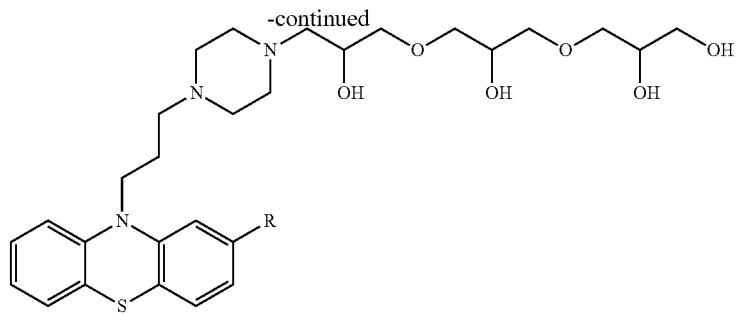

R = Cl, 33a
R = CF₃, 33b

As shown in Scheme 7 above, benzyl protected triglycerol is mono protected with THP to provide Compound 28. Compound 28 can be further protected to provide Compound 29. The THP can be removed under standard protocol to provide Compound 30, which can be subsequently tosylated to provide Compound 31. Global deprotection can be accomplished with H2 and Pd/C to provide Compound 32. Compound 32 is coupled with NDP or NDT under basic conditions to provide NDP-[CH₂CH(OH)CH₂O]₃—H or NDT-[CH₂CH(OH)CH₂O]₃—H.

The invention having now been described by way of written description, those of skill in the art will recognize that the invention can be practiced in a variety of embodiments and that the foregoing description and examples below are for purposes of illustration and not limitation of the claims that follow.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended. It is to be further understood that resort may be had to various other embodiments, modifications, and equivalents thereof which may suggest themselves to those skilled in the art without departing from the spirit of the present disclosure and/or scope of the appended claims.

Example 1: Preparation of Compounds 1-1, 1-2, 1-3, 1-4, 1-5, 2-1, 2-2, 2-3, 2-4, 3-1, 3-2, 3-3 and 3-4 mPEGs, such as H—[CH₂CH₂O]$_n$—CH₃ (n=3, 6, 9 or 12) were prepared according to WO2002098949A1, and H—[CH₂CH₂O]₁₆—CH₃ was purchased from Alfa Aesar. TFP, PCP, NDP and NDT were prepared according to a published procedure (U.S. Pat. No. 2,902,484). Scheme 1 above shows the preparation of compounds 1-1, 1-2, 1-3, 1-4, 1-5, 2-1, 2-2, 2-3, 2-4, 3-1, 3-2, 3-3 and 3-4.

Example 2: General Procedure for Preparing Ts-O—[CH₂CH₂O]$_n$—CH₃ (n=3, 6, 12, 16 or 9; Compounds 1-1, 1-2, 1-3, 1-4 or 1-5)

To a solution of H—[CH₂CH₂O]$_n$—CH₃ (n=3, 6, 12, 16 or 9, 2.00 mmol) in dichloromethane (DCM, 6 mL) or tetrahydrofuran (THF)/water (4.6 mL/1.4 mL) was added tosyl chloride (TsCl, 2.10 mmol) and potassium hydroxide (8.02 mmol) at 0° C. The reaction mixture was stirred at room temperature for 22 h then diluted with DCM (30 mL) and H₂O (20 mL). The aqueous layer was separated and extracted with DCM (30 mL×2). The combined organic layers were washed with brine, dried over MgSO₄, filtered and evaporated under reduced pressure. Purification of the residue on a silica gel column afforded Ts-O—[CH₂CH₂O]$_n$—CH₃ (n=3, 6, 12, 16 or 9, Compounds 1-1, 1-2, 1-3, 1-4 or 1-5).

Ts-O—[CH₂CH₂O]₃—CH₃ (Compound 1-1): $^1$H NMR (400 MHz, CDCl₃) δ 2.43 (s, 3H), 3.35 (s, 3H), 3.50-3.53 (m, 2H), 3.57-3.61 (m, 8H), 3.67 (t, J=4.8 Hz, 2H), 4.14 (t, J=4.8 Hz, 2H), 7.31 (d, J=8.0 Hz, 2H), 7.78 (d, J=8.0 Hz, 2H).

Ts-O—[CH₂CH₂O]₆—CH₃ (Compound 1-2): $^1$H NMR (400 MHz, CDCl₃) δ 2.42 (s, 3H), 3.35 (s, 3H), 3.51-3.70 (m, 22H), 4.13 (d, J=4.8 Hz, 2H), 7.31 (d, J=8.0 Hz, 2H), 7.77 (d, J=8.0 Hz, 2H).

Ts-O—[CH₂CH₂O]₁₂—CH₃ (Compound 1-3): $^1$H NMR (400 MHz, CDCl₃) δ 2.41 (s, 3H), 3.34 (s, 3H), 3.50-3.80 (m, 46H), 4.12 (t, J=4.8 Hz, 2H), 7.31 (d, J=8.0 Hz, 2H), 7.76 (d, J=8.0 Hz, 2H).

Ts-O—[CH₂CH₂O]₁₆—CH₃ (Compound 1-4): $^1$H NMR (400 MHz, CDCl₃) δ 2.42 (s, 3H), 3.35 (s, 3H), 3.50-3.80 (m, 62H), 4.13 (t, J=4.8 Hz, 2H), 7.32 (d, J=8.0 Hz, 2H), 7.77 (d, J=8.0 Hz, 2H).

Ts-O—[CH₂CH₂O]₉—CH₃ (Compound 1-5): $^1$H NMR (400 MHz, CDCl₃) δ 2.42 (s, 3H), 3.35 (s, 3H), 3.51-3.67 (m, 34H), 4.13 (t, J=4.8 Hz, 2H), 7.31 (d, J=8.0 Hz, 2H), 7.77 (d, J=8.0 Hz, 2H).

Example 3: General Procedure for Preparing 4-Nitrophenyl-[CH₂CH₂O]$_n$—CH₃ Carbonates (n=3, 6, 12 or 16; Compounds 2-1, 2-2, 2-3 or 2-4)

To a stirred solution of CH₃O—[CH₂CH₂O]$_n$—H (n=3, 6, 12 or 16, 2.00 mmol) and pyridine (Py, 4.0 mmol) in anhydrous DCM (5 mL) was added 4-nitrophenyl chloroformate (2.80 mmol) in one portion at 0° C. under argon. The reaction mixture was stirred at room temperature for 5 h. The mixture was diluted with DCM (40 mL), washed with 1N HCl (20 mL) and brine, dried over MgSO₄ and filtered. The solvent was evaporated under reduced pressure. Purification of the residue on a silica gel column afforded 4-nitrophenyl —[CH₂CH₂O]$_n$—CH₃ carbonate (n=3, 6, 12 or 16; Compounds 2-1, 2-2, 2-3 or 2-4).

4-nitrophenyl-[CH$_2$CH$_2$O]$_3$—CH$_3$ carbonate (Compound 2-1): $^1$H NMR (400 MHz, CDCl$_3$) δ 3.35 (s, 3H), 3.53-3.55 (m, 2H), 3.63-3.70 (m, 6H), 3.78-3.81 (m, 2H), 4.41-4.43 (m, 2H), 7.37 (d, J=9.2 Hz, 2H), 8.26 (d, J=9.2 Hz, 2H).

4-nitrophenyl-[CH$_2$CH$_2$O]$_6$—CH$_3$ carbonate (Compound 2-2): $^1$H NMR (400 MHz, CDCl$_3$) δ 3.35 (s, 3H), 3.51-3.53 (m, 2H), 3.60-3.69 (m, 18H), 3.78-3.80 (m, 2H), 4.41-4.43 (m, 2H), 7.37 (d, J=9.2 Hz, 2H), 8.26 (d, J=9.2 Hz, 2H).

4-nitrophenyl-[CH$_2$CH$_2$O]$_{12}$—CH$_3$ carbonate (Compound 2-3): $^1$H NMR (400 MHz, CDCl$_3$) δ 3.35 (s, 3H), 3.52-3.80 (m, 46H), 4.41-4.43 (m, 2H), 7.38 (d, J=7.2 Hz, 2H), 8.27 (d, J=7.2 Hz, 2H).

4-nitrophenyl-[CH$_2$CH$_2$O]$_{16}$—CH$_3$ carbonate (Compound 2-4): $^1$H NMR (400 MHz, CDCl$_3$) δ 3.35 (s, 3H), 3.52-3.80 (m, 62H), 4.41-4.43 (m, 2H), 7.37 (d, J=8.8 Hz, 2H), 8.27 (d, J=8.8 Hz, 2H).

Example 4: General Procedure for Preparing Acetic Acid-CH$_2$O—[CH$_2$CH$_2$O]$_n$—CH$_3$ (n=3, 6, 12 or 16; Compounds 3-1, 3-2, 3-3 or 3-4)

To a solution of CH$_3$O—[CH$_2$CH$_2$O]$_n$—H (n=3, 6, 12 or 16; 12.18 mmol) and bromoacetic acid (13.4 mmol) in THF (24 mL) was added sodium hydride (NaH, 57-63% in oil, 48.72 mmol). The reaction mixture was stirred for 5 h at room temperature. The excess sodium hydride was quenched by the addition of 1N hydrochloric acid (50 mL). The organic solvent was evaporated under reduced pressure. The aqueous solution was extracted with ethyl acetate (30 mL×3). The combined organic layers were dried with MgSO$_4$ and concentrated under reduced pressure to afford acetic acid-CH$_2$O—[CH$_2$CH$_2$O]$_n$—CH$_3$ (n=3, 6, 12 or 16; Compounds 3-1, 3-2, 3-3 or 3-4).

acetic acid-CH$_2$O—[CH$_2$CH$_2$O]$_3$—CH$_3$ (Compound 3-1): $^1$H NMR (400 MHz, CDCl$_3$) δ 3.37 (s, 3H), 3.55-3.73 (m, 12H), 4.12 (s, 2H).

acetic acid-CH$_2$O—[CH$_2$CH$_2$O]$_6$—CH$_3$ (Compound 3-2): $^1$H NMR (400 MHz, CDCl$_3$) δ 3.36 (s, 3H), 3.52-3.77 (m, 24H), 4.12 (s, 2H).

acetic acid-CH$_2$O—[CH$_2$CH$_2$O]$_{12}$—CH$_3$ (Compound 3-3): $^1$H NMR (400 MHz, CDCl$_3$) δ 3.26 (s, 3H), 3.43-3.62 (m, 48H), 4.03 (s, 2H).

acetic acid-CH$_2$O—[CH$_2$CH$_2$O]$_{16}$—CH$_3$ (Compound 3-4): $^1$H NMR (400 MHz, CDCl$_3$) δ 3.35 (s, 3H), 3.45-3.79 (m, 64H), 4.11 (s, 2H).

Example 5: Preparation of NDP or NDT Conjugates

Scheme 2 above shows the preparation of NDP or NDT conjugates.

Example 6

To a stirred solution of NDP or NDT (3.99 mmol) and Ts-O—[CH$_2$CH$_2$O]$_n$—CH$_3$ (4.30 mmol, Compound 1-1 (n=3), 1-2 (n=6), 1-3 (n=12) or 1-4 (n=16)) in dry acetone or acetonitrile (CH$_3$CN) (50 mL) was added potassium carbonate (K$_2$CO$_3$, 20 mmol) at room temperature under argon. After refluxing (rfx) for 20 h, the mixture was diluted with acetone and the precipitation was removed by filtration. The solvent was evaporated under reduced pressure. The residue was purified on a silica gel column to afford Compound 4-1a, 4-2a, 4-3a, 4-4a, 4-1b, 4-2b, 4-3b or 4-4b.

Compound 4-1a: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 12H), 3.92 (t, J=6.8 Hz, 2H), 6.82-7.14 (m, 7H).

Compound 4-2a: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 24H), 3.92 (t, J=6.8 Hz, 2H), 6.82-7.14 (m, 7H).

Compound 4-3a: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 48H), 3.92 (t, J=6.8 Hz, 2H), 6.82-7.14 (m, 7H).

Compound 4-4a: $^1$H NMR (400 MHz, CDCl$_3$) δ 1.91 (t, J=6.8 Hz, 2H), 2.44 (t, J=6.8 Hz, 8H), 2.55 (t, J=6.8 Hz, 2H), 3.35 (s, 3H), 3.51-3.70 (m, 64H), 3.86 (t, J=6.8 Hz, 2H), 6.82-7.12 (m, 7H).

Compound 4-1b: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 12H), 3.92 (t, J=6.8 Hz, 2H), 6.88-7.18 (m, 7H).

Compound 4-2b: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 24H), 3.92 (t, J=6.8 Hz, 2H), 6.88-7.18 (m, 7H).

Compound 4-3b: $^1$H NMR (400 MHz, CDCl$_3$) δ 1.91 (t, J=6.8 Hz, 2H), 2.45 (t, J=6.8 Hz, 8H), 2.57 (t, J=6.8 Hz, 2H), 3.35 (s, 3H), 3.51-3.68 (m, 48H), 3.92 (t, J=6.8 Hz, 2H), 6.88-7.18 (m, 7H).

Compound 4-4b: $^1$H NMR (400 MHz, CDCl$_3$) δ 1.91 (t, J=6.8 Hz, 2H), 2.45 (t, J=6.8 Hz, 8H), 2.54 (t, J=6.8 Hz, 2H), 3.35 (s, 3H), 3.44-3.80 (m, 64H), 3.92 (t, J=6.8 Hz, 2H), 6.88-7.17 (m, 7H).

Example 7

To a stirred solution of NDP or NDT (3.0 mmol) and 4-nitrophenyl-[CH$_2$CH$_2$O]$_n$—CH$_3$ carbonate (2.5 mmol, Compound 2-1 (n=3), 2-2 (n=6), 2-3 (n=12) or 2-4 (n=16)) in THF (10 mL) was added diisopropylethylamine (DIPEA) (4.6 mmol) at room temperature under argon, and the reaction mixture was refluxed for 20 h. The solvent was evaporated under reduced pressure. The residue was purified on a silica gel column to afford Compound 5-1a, 5-2a, 5-3a, 5-4a, 5-1b, 5-2b, 5-3b or 5-4b.

NDP-CO—O—[CH$_2$CH$_2$O]$_3$—CH$_3$ (Compound 5-1a): $^1$H NMR (400 MHz, CDCl$_3$) δ 1.92 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 10H), 3.91 (t, J=6.8 Hz, 2H), 4.19-4.21 (m, 2H), 6.83-7.15 (m, 7H).

NDP-CO—O—[CH$_2$CH$_2$]$_6$—CH$_3$ (Compound 5-2a): $^1$H NMR (400 MHz, CDCl$_3$) δ 1.92 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 22H), 3.91 (t, J=6.8 Hz, 2H), 4.19-4.21 (m, 2H), 6.83-7.15 (m, 7H).

NDP-CO—O—[CH$_2$CH$_2$O]$_{12}$—CH$_3$ (Compound 5-3a): $^1$H NMR (400 MHz, CDCl$_3$) δ 1.92 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 46H), 3.91 (t, J=6.8 Hz, 2H), 4.19-4.21 (m, 2H), 6.83-7.15 (m, 7H).

NDP-CO—O—[CH$_2$CH$_2$O]$_{16}$—CH$_3$ (Compound 5-4a): $^1$H NMR (400 MHz, CDCl$_3$) δ 1.92 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 62H), 3.91 (t, J=6.8 Hz, 2H), 4.19-4.21 (m, 2H), 6.83-7.15 (m, 7H).

NDT-CO—O—[CH$_2$CH$_2$O]$_3$—CH$_3$ (Compound 5-1b): $^1$H NMR (400 MHz, CDCl$_3$) δ 1.91 (t, J=6.8 Hz, 2H), 2.30-2.36 (m, 4H), 2.46 (t, J=6.8 Hz, 2H), 3.35 (s, 3H), 3.39-3.42 (m, 4H), 3.51-3.68 (m, 10H), 3.95 (t, J=6.8 Hz, 2H), 4.19-4.21 (m, 2H), 6.88-7.18 (m, 7H).

NDT-CO—O—[CH$_2$CH$_2$O]$_6$—CH$_3$ (Compound 5-2b): $^1$H NMR (400 MHz, CDCl$_3$) δ 1.90 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 22H), 3.95 (t, J=6.8 Hz, 2H), 4.19-4.21 (m, 2H), 6.88-7.18 (m, 7H).

NDT-CO—O—[CH$_2$CH$_2$O]$_{12}$—CH$_3$ (Compound 5-3b): $^1$H NMR (400 MHz, CDCl$_3$) δ 1.90 (t, J=6.8 Hz, 2H), 2.30-2.36 (m, 4H), 2.45 (t, J=6.8 Hz, 2H), 3.35 (s, 3H), 3.39-3.42 (m, 4H), 3.51-3.68 (m, 46H), 3.95 (t, J=6.8 Hz, 2H), 4.19-4.21 (m, 2H), 6.88-7.18 (m, 7H).

NDT-CO—O—[CH$_2$CH$_2$O]$_{16}$—CH$_3$ (Compound 5-4b): $^1$H NMR (400 MHz, CDCl$_3$) δ 1.90 (t, J=6.8 Hz, 2H), 2.30-2.36 (m, 4H), 2.45 (t, J=6.8 Hz, 2H), 3.35 (s, 3H), 3.37-3.40 (m, 4H), 3.51-3.68 (m, 62H), 3.96 (t, J=6.8 Hz, 2H), 4.17-4.20 (m, 2H), 6.88-7.18 (m, 7H).

Example 8

To a solution of NDP or NDT (2.77 mmol) and acetic acid-CH$_2$O—[CH$_2$CH$_2$O]$_n$—CH$_3$ (3.66 mmol, Compound 3-1 (n=3), 3-2 (n=6), 3-3 (n=12) or 3-4 (n=16)) in DCM (14 mL) was added 1-Ethyl-3-(3-dimethylaminopropyl)carbodiimide (EDC, 4.1 mmol) and 4-dimethylaminopyridine (DMAP, 0.262 mmol) at 0° C. The resulting solution was stirred at room temperature for 21 h, poured into water and extracted with DCM. The combined organic layers were washed with brine, dried over MgSO$_4$ and filtered. The filtrate was concentrated under reduced pressure. Purification of the residue on a silica gel column afforded Compound 6-1a, 6-2a, 6-3a, 6-4a, 6-1b, 6-2b, 6-3b or 6-4b.

NDP-CO—[CH$_2$CH$_2$O]$_3$—CH$_3$ (Compound 6-1a): $^1$H NMR (400 MHz, CDCl$_3$) δ 1.91 (t, J=6.8 Hz, 2H), 2.35-2.47 (m, 6H), 3.35-3.39 (m, 5H), 3.51-3.63 (m, 14H), 3.91 (t, J=6.8 Hz, 2H), 4.15 (s, 2H), 6.88-7.19 (m, 7H).

NDP-CO—[CH$_2$CH$_2$O]$_6$—CH$_3$ (Compound 6-2a): $^1$H NMR (400 MHz, CDCl$_3$) δ 1.90 (t, J=6.8 Hz, 2H), 2.36-2.46 (m, 6H), 3.35-3.41 (m, 5H), 3.52-3.64 (m, 26H), 3.91 (t, J=6.8 Hz, 2H), 4.15 (s, 2H), 6.83-7.14 (m, 7H).

NDP-CO—[CH$_2$CH$_2$O]$_{12}$—CH$_3$ (Compound 6-3a): $^1$H NMR (400 MHz, CDCl$_3$) δ 1.90 (t, J=6.8 Hz, 2H), 2.34-2.46 (m, 6H), 3.35-3.41 (m, 5H), 3.51-3.63 (m, 50H), 3.91 (t, J=6.8 Hz, 2H), 4.15 (s, 2H), 6.83-7.13 (m, 7H).

NDP-CO—[CH$_2$CH$_2$O]$_{16}$—CH$_3$ (Compound 6-4a): $^1$H NMR (400 MHz, CDCl$_3$) δ 1.90 (t, J=6.8 Hz, 2H), 2.34-2.47 (m, 6H), 3.35-3.38 (m, 5H), 3.50-3.62 (m, 66H), 3.91 (t, J=6.8 Hz, 2H), 4.15 (s, 2H), 6.83-7.13 (m, 7H).

NDT-CO—[CH$_2$CH$_2$O]$_3$—CH$_3$ (Compound 6-1b): $^1$H NMR (400 MHz, CDCl$_3$) δ 1.91 (t, J=6.8 Hz, 2H), 2.35-2.47 (m, 6H), 3.35-3.39 (m, 5H), 3.51-3.63 (m, 14H), 3.91 (t, J=6.8 Hz, 2H), 4.15 (s, 2H), 6.88-7.19 (m, 7H).

NDT-CO—[CH$_2$CH$_2$O]$_6$—CH$_3$ (Compound 6-2b): $^1$H NMR (400 MHz, CDCl$_3$) δ 1.91 (t, J=6.8 Hz, 2H), 2.35-2.47 (m, 6H), 3.35-3.39 (m, 5H), 3.50-3.64 (m, 26H), 3.91 (t, J=6.8 Hz, 2H), 4.15 (s, 2H), 6.88-7.18 (m, 7H).

NDT-CO—[CH$_2$CH$_2$O]$_{12}$—CH$_3$ (Compound 6-3b): $^1$H NMR (400 MHz, CDCl$_3$) δ 1.90 (t, J=6.8 Hz, 2H), 2.34-2.47 (m, 6H), 3.35-3.39 (m, 5H), 3.51-3.63 (m, 50H), 3.91 (t, J=6.8 Hz, 2H), 4.15 (s, 2H), 6.88-7.19 (m, 7H).

NDT-CO—[CH$_2$CH$_2$O]$_{16}$—CH$_3$ (Compound 6-4b): $^1$H NMR (400 MHz, CDCl$_3$) δ 1.90 (t, J=6.8 Hz, 2H), 2.34-2.47 (m, 6H), 3.35-3.38 (m, 5H), 3.50-3.62 (m, 66H), 3.91 (t, J=6.8 Hz, 2H), 4.15 (s, 2H), 6.88-7.18 (m, 7H).

Example 9: Procedure for Preparing Ts-O—[CH$_2$CH(OCH$_3$)CH$_2$O]$_m$—CH$_3$

Scheme 3 above shows the preparation of Ts-O—[CH$_2$CH(OCH$_3$)CH$_2$O]$_m$—CH$_3$. Compound 7 was methylated under basic conditions to provide Compound 8. Global deprotection was accomplished under acidic conditions to provide Compound 9. Silyl protection of the terminal alcohols, followed by methylation of Compound 10 under standard protocol provided Compound 11. Global deprotection with TBAF provided Compound 12, followed by mono THP protection afforded Compound 13. Methylation of Compound 13, followed by deprotection under acidic conditions provided Compound 15. Tosylation of Compound 15 provided Ts-O—[CH$_2$CH(OCH$_3$)CH$_2$O]$_3$—CH$_3$ (Compound 16).

Example 10: Preparation of Compound 7 (1,2,10,11-bis(isopropylidenedioxy)-4,8-dioxaundecan-6-ol)

Compound 7 was prepared from triglycerol (HO—[CH$_2$CH(OH)CH$_2$O]$_3$—H) according to a published procedure (Nemoto et al., Chem. Lett., 2010, 39, 856-857). $^1$H NMR (400 MHz, [D$_6$]acetone): δ 1.28 (s, 6H, CH$_3$), 1.33 (s, 6H, CH$_3$), 2.83 (s, 1H, OH), 3.50 (ddd, J=31.8, 10.1, 5.5 Hz, ddd, J=17.4, 11.9, 6.3 Hz, 8H), 3.75 (td, J=4.9, 1.5 Hz, 1H), 3.69 (dd, J=8.2, 6.3 Hz, 2H), 4.00 (dd, J=8.2, 6.4 Hz, 2H), 3.84 (m, 1H), 4.19 (q, J=11.9, 6.3 Hz, 2H).

Example 11: Preparation of Compound 8

To a solution of Compound 7 (10 g, 31.21 mmol) in THF (104 mL) was added NaH (2.25 mg, 56.25 mmol) at 0° C. After the mixture was stirred for 30 minutes at room temperature, methyl iodide (CH$_3$I, 2.6 mL, 41.76 mmol) was added slowly at 0° C. The resulting solution was stirred at room temperature for 18 h, poured into water and extracted with DCM. The combined organic layers were washed with brine, dried over MgSO$_4$ and filtered. The filtrate was concentrated under reduced pressure. Purification of the residue on a silica gel column eluted with EtOAc/hexane (v/v=1:2 and 1:1) afforded Compound 8 (10.2 g, 98% yield). $^1$H NMR (400 MHz, CDCl$_3$): δ 1.33 (s, 6H), 1.39 (s, 6H), 3.73-3.33 (m, 14H), 4.04-4.01 (m, 2H), 4.26-4.22 (m, 2H).

Example 12: Preparation of Compound 9

To a solution of Compound 8 (10.2 g, 30.5 mmol) in MeOH (60 mL) was added DOWEX H+(4.8 g) at room temperature. The resulting solution was stirred at reflux for 17 h and filtered. The filtrate was concentrated under reduced pressure to afford Compound 9 (7.66 g, 99% yield). $^1$H NMR (400 MHz, CD$_3$OD): δ 3.31-3.75 (m, 18H).

Example 13: Preparation of Compound 10

To a solution of Compound 9 (7.66 g, 30.12 mmol) in DCM (280 mL) was added trimethylamine (Et$_3$N, 17.6 mL, 126.27 mmol) and 4-dimethylaminopyridine (DMAP, 1.84 g, 15.06 mmol) at room temperature and then tert-butyl (chloro)diphenylsilane (TBDPSCl, 16.66 mL, 64.07 mmol) at 0° C. The resulting solution was stirred at room temperature for 18 h, poured into water and extracted with DCM. The combined organic layers were washed with brine, dried over MgSO$_4$ and filtered. The filtrate was concentrated under reduced pressure. Purification of the residue on a silica gel column eluted with EtOAc/hexane (v/v=1:3, 1:2 and 1:1) afforded Compound 10 (16.9 g, 77% yield). Chemical shifts of $^1$H NMR (400 MHz, CDCl$_3$): δ 1.01 (s, 18H), 2.72 (s, 1H), 3.88-3.30 (m, 19H), 7.42-7.34 (m, 12H), 7.64-7.62 (m, 8H).

Example 14: Preparation of Compound 11

To a solution of Compound 10 (16.9 g, 23.11 mmol) in THF (80 mL) was added NaH (3 g, 75 mmol) at 0° C. After the mixture had been stirred for 30 minutes at room temperature, methyl iodide (3.6 mL, 57.83 mmol) was added slowly at 0° C. The resulting solution was stirred at room temperature for 20 h, poured into water and extracted with DCM. The combined organic layers were washed with brine, dried over $Na_2SO_4$ and filtered. The filtrate was concentrated under reduced pressure. Purification of the residue on a silica gel column eluted with EtOAc/hexane (v/v=2:7) afforded Compound 11 (15.3 g, 87% yield). $^1$H NMR (400 MHz, $CDCl_3$): δ 1.01 (s, 18H), 3.27-3.75 (m, 24H), 7.34-7.40 (m, 12H), 7.64-7.66 (m, 8H).

Example 15: Preparation of Compound 12

To a solution of Compound 11 (15.3 g, 20.15 mmol) in THF (100 mL) was added slowly a tetrabutylammonium fluoride (TBAF) solution 1.0 M in THF (60 mL, 60.0 mmol) at 0° C. The solution was stirred at room temperature for 7 h. The resulting solution was concentrated under reduced pressure. Purification of the residue on a silica gel column eluted with EtOAc/hexane (v/v=1:1), EtOAc/acetone (v/v=1:4) and DCM/MeOH (v/v=9:1) afforded Compound 12 (5.5 g, 97% yield). $^1$H NMR (400 MHz, $CDCl_3$): δ 3.28-3.73 (m, 26H).

Example 16: Preparation of Compound 13

To a stirred solution of Compound 12 (5.03 g, 17.82 mmol) in DCM (37 mL) was added slowly dihydropyran (DHP, 1.3 mL, 16.88 mmol) and p-toluenesulfonic acid (pTSA, 598 mg, 3.14 mmol) at 0° C. under argon. The solution was stirred at room temperature for 22 h, poured into water and extracted with $NaHCO_{3(aq)}$ and DCM. The combined organic layers were washed with brine, dried over $MgSO_4$ and filtered. The filtrate was concentrated under reduced pressure. Purification of the residue on a silica gel column eluted with acetone:hexane (v/v=1:1.5 and 1:1) and MeOH:DCM (v/v=1:9) afforded Compound 13 (2.98 g, 57% yield). $^1$H NMR (400 MHz, $CDCl_3$): δ 1.59-1.80 (m, 6H), 2.35-2.36 (m, 1H), 3.33-3.82 (m, 26H), 4.58 (m, 1H).

Example 17: Preparation of Compound 14

To a solution of Compound 13 (3.2 g, 8.73 mmol) in THF (44 mL) was added NaH (700 mg, 17.5 mmol) at 0° C. After the mixture had been stirred for 30 minutes at room temperature, $CH_3I$ (0.82 mL, 13.17 mmol) was added slowly at 0° C. The solution was stirred at room temperature for 18 h, poured into water and extracted with DCM. The combined organic layers were washed with brine, dried over $MgSO_4$ and filtered. The filtrate was concentrated under reduced pressure. Purification of the residue on a silica gel column eluted with EtOAc/hexane (v/v=1:1) and acetone/hexane (v/v=1:2) afforded Compound 14 (3.27 g, 98% yield). $^1$H NMR (400 MHz, $CDCl_3$): δ 1.51-1.81 (m, 6H), 3.33-3.82 (m, 29H), 4.58 (m, 1H).

Example 18: Preparation of Compound 15

To a solution of Compound 14 (3.27 g, 8.59 mmol) in MeOH (40 mL) was added pTSA (165 mg, 0.87 mmol) at 0° C. The resulting solution was stirred at room temperature for 20 h, poured into water and extracted with $NaHCO_{3(aq)}$ and DCM. The combined organic layers were washed with brine, dried over $MgSO_4$ and filtered. The filtrate was concentrated under reduced pressure to afford Compound 15 as colorless oil (2.39 g, 94% yield). $^1$H NMR (400 MHz, $CDCl_3$): δ 2.31-2.32 (m, 1H), 3.33-3.82 (m, 27H).

Example 19: Preparation of Compound 16

To a solution of Compound 15 (529 mg, 1.78 mmol) in THF (6 mL) and water (2 mL) was added KOH (410 mg, 6.21 mmol) and TsCl (510 mg, 2.68 mmol) at 0° C. The solution was stirred at room temperature for 17 h, poured into water and extracted with DCM. The combined organic layers were washed with brine, dried over $MgSO_4$ and filtered. The filtrate was concentrated under reduced pressure. Purification of the residue on a silica gel column eluted with EtOAc/hexane (v/v=1.5:1 and 4:1) afforded Compound 16 (Ts-O—[$CH_2CH(OCH_3)CH_2O$]$_3$—$CH_3$; 780 mg, 97% yield). $^1$H NMR (400 MHz, $CDCl_3$): δ 2.43 (s, 3H), 3.30-3.61 (m, 25H), 4.00-4.04 (m, 1H), 4.12-4.15 (m, 1H), 7.32 (d, 2H), 7.77 (d, 2H).

Example 20: Procedures for Preparing Ts-O—[$CH_2CH_2O$]$_n$—[$C_H2CH(OCH_3)CH_2O$]$_3$—$CH_3$ (Compound 19-1 (n=3) and Compound 19-2 (n=9)

Scheme 4 above shows the preparation of Ts-O—[$CH_2CH_2O$]$_n$—[$CH_2CH(OCH_3)CH_2O$]$_3$—$CH_3$ (Compound 19-1 (n=3) and Compound 19-2 (n=9). Compound 15 was coupled under basic conditions to provide Compound 17. Deprotection was accomplished under acidic conditions to provide Compound 18-1. Tosylation of Compound 18-1 provided Compound 19-1. Coupling under basic conditions provided Compound 20. Deprotection using H2 and Pd/C provided Compound 18-2. Tosylation of Compound 18-2 provided Compound 19-2.

Example 21: Preparation of Compound 17

To a solution of Compound 15 (1.8 g, 6.07 mmol) in THF (20 mL) was added NaH (465 mg, 11.63 mmol) at 0° C. After the mixture had been stirred for 30 minutes at room temperature, 2-(2-(2-(tetrahydro-2H-pyran-2-yloxy)ethoxy)ethoxy)ethyl 4-methylbenzenesulfonate (Ts-O—[$CH_2CH_2O$]$_3$-THP, 3.58 mL, 9.22 mmol) in THF (10 mL) was added slowly at 0° C. The solution was stirred at room temperature for 20 h, poured into water and extracted with DCM. The combined organic layers were washed with brine, dried over $MgSO_4$ and filtered. The filtrate was concentrated under reduced pressure. Purification of the crude product on a silica gel column eluted with EtOAc/hexane (v/v=3:1) and acetone/hexane (v/v=1:2 and 1:1) afforded Compound 17 (2.78 g, 89% yield). $^1$H NMR (400 MHz, $CDCl_3$): δ 1.55-1.82 (m, 6H), 3.33-3.87 (m, 41H), 4.60-4.61 (m, 1H).

Example 22: Preparation of Compound 18-1

To a solution of Compound 17 (2.78 g, 5.42 mmol) in MeOH (30 mL) was added pTSA (110 mg, 0.578 mmol) at 0° C. The resulting solution was stirred at room temperature for 20 h, poured into water and extracted with $NaHCO_{3(aq)}$ and DCM. The combined organic layers were washed with brine, dried over $MgSO_4$ and filtered. The filtrate was concentrated under reduced pressure to afford Compound 18-1 (2.24 g, 97% yield). $^1$H NMR (400 MHz, $CDCl_3$): δ 3.33-3.71 (m, 37H), 2.00 (m, 1H).

Example 23: Preparation of Compound 19-1

To a solution of Compound 18-1 (2.24 g, 5.23 mmol) in THF (22 mL) and water (7 mL) was added KOH (1.38 g, 20.9 mmol) and TsCl (1.5 g, 7.87 mmol) at 0° C. The solution was stirred at room temperature for 18 h, poured into water and extracted with DCM. The combined organic layers were washed with brine, dried over $MgSO_4$ and filtered. The filtrate was concentrated under reduced pressure. Purification of the resulting residue on a silica gel column eluted with EtOAc/hexane (v/v=3:1 and 4:1) and acetone/DCM (v/v=1:2) afforded Compound 19-1 (2.95 g, 97% yield). $^1$H NMR (400 MHz, $CDCl_3$): δ 2.42 (s, 3H), 3.33-3.67 (m, 10H), 3.33-3.67 (m, 37H), 4.13 (t, J=4.8 Hz, 2H), 7.31 (d, 2H), 7.77 (d, 2H).

Example 24: Preparation of Compound 20

To a solution of 1-phenyl-2,5,8,11,14,17-hexaoxanonadecan-19-ol (Bn-O—[$CH_2CH_2O$]$_6$—H, 913 mg, 2.45 mmol) in THF (8 mL) was added NaH (202 mg, 5.05 mmol) at 0° C. The mixture was stirred for 30 minutes at room temperature. To the mixture Compound 19-1 (1.74 g, 2.99 mmol) in THF (5 mL) was added slowly at 0° C. The solution was stirred at 35° C. for 20 h, poured into water and extracted with DCM. The combined organic layers were washed with brine, dried over $MgSO_4$ and filtered. The filtrate was concentrated under reduced pressure. Purification of the residue on a silica gel column eluted with acetone/DCM (v/v=1:2) and MeOH/DCM (v/v=1:15, 1:10 and 1:8) afforded Compound 20 (1.88 g, 98% yield). $^1$H NMR (400 MHz, $CDCl_3$): δ 3.33-3.65 (m, 63H), 4.54 (s, 2H), 7.26-7.32 (m, 5H).

Example 25: Preparation of Compound 18-2

Compound 20 (1.88 g, 0.085 mmol) in MeOH (1.8 mL) was treated with 10% palladium on charcoal (10 weight %, 200 mg) under hydrogen at atmospheric pressure and room temperature for 18 h. The catalyst was removed by filtration through Celite. The filtrate was concentrated under reduced pressure to afford Compound 18-2 (1.64 g, 99% yield). $^1$H NMR (400 MHz, $CDCl_3$): δ 3.33-3.71 (m, 63H).

Example 26: Preparation of Compound 19-2

To a solution of Compound 18-2 (1.64 g, 2.37 mmol) in THF (9 mL) and water (3 mL) was added KOH (619 g, 9.38 mmol) and TsCl (727 mg, 3.81 mmol) at 0° C. The resulting solution was stirred at room temperature for 19 h, poured into water and extracted with DCM. The combined organic layers were washed with brine, dried over $MgSO_4$ and filtered. The filtrate was concentrated under reduced pressure. Purification of the residue on a silica gel column eluted with EtOAC/acetone (v/v=3:1) and MeOH/DCM (v/v=1:15, 1:10 and 1:8) afforded Compound 19-2 (1.85 g, 93% yield). $^1$H NMR (400 MHz, $CDCl_3$): δ 2.42 (s, 3H), 3.33-3.67 (m, 61H), 4.13 (t, J=4.4 Hz, 2H), 7.31 (d, 2H), 7.77 (d, 2H).

Example 27: General Procedure for Preparing C H$_3$—O—[$CH_2CH_2O$]$_n$—[$CH_2CH(OCH_3)CH_2O$]$_3$-Ts (Compound 23-1 (n=3) and 23-2 (n=9))

Scheme 5 above shows the general preparation of $CH_3$—O—[$CH_2CH_2O$]$_n$—[$CH_2CH(OCH_3)CH_2O$]$_3$-Ts (Compound 23-1 (n=3) and 23-2 (n=9)). Compound 13 was coupled under basic conditions to provide Compound 21-1 (n=3) or 21-2 (n=9). Deprotection was accomplished under acidic conditions to provide Compound 22-1 (n=3) or 22-2 (n=9). Tosylation of Compound 22-1 (n=3) or 22-2 (n=9) provided Compound 23-1 (n=3) or 23-2 (n=9) respectively.

Example 28: General Procedure for Preparing Compound 21-1 and 21-2

To a solution of Compound 13 (1.45 g, 3.96 mmol) in THF (15 mL) was added NaH (320 mg, 8.0 mmol) at 0° C. After the mixture had been stirred for 30 minutes at room temperature, Compound 1-1 (n=3) or 1-5 (n=9) (5.97 mmol) in THF (5 mL) was added slowly at 0° C. The solution was stirred at room temperature for 20 h, poured into water and extracted with DMF. The combined organic layers were washed with brine, dried over $MgSO_4$ and filtered. The filtrate was concentrated under reduced pressure. Purification of the residue on a silica gel column afforded Compound 21-1 or 21-2.

Compound 21-1: $^1$H NMR (400 MHz, $CDCl_3$): δ 1.55-1.68 (m, 6H), 3.33-3.81 (m, 41H), 4.58 (m, 1H).

Compound 21-2: $^1$H NMR (400 MHz, $CDCl_3$): δ 1.54-1.68 (m, 6H), 3.33-3.80 (m, 65H), 4.58 (m, 1H).

Example 29: General Procedure for Preparing Compound 22-1 and 22-2

To a solution of Compound 21-1 or 21-2 (3.76 mmol) in MeOH (19 mL) was added pSTA (90 mg, 0.47 mmol) at 0° C. The resulting solution was stirred at room temperature for 20 h, poured into water and extracted with $NaHCO_{3(aq)}$ and DCM. The combined organic layers were washed with brine, dried over $MgSO_4$ and filtered. The filtrate was concentrated under reduced pressure to afford Compound 22-1 or 22-2.

Compound 22-1: $^1$H NMR (400 MHz, $CDCl_3$): δ 2.45 (m, 1H), 3.29-3.72 (m, 39H).

Compound 22-2: $^1$H NMR (400 MHz, $CDCl_3$): δ 2.46 (m, 1H), 3.33-3.70 (m, 63H).

Example 30: General Procedure for Preparing Compound 23-1 and 23-2

To a solution of Compound 22-1 or 22-2 (3.73 mmol) in THF (15 mL) and water (5 mL) was added KOH (1.0 g, 15.22 mmol) and TsCl (1.09 g, 5.72 mmol) at 0° C. The resulting solution was stirred at room temperature for 18 h, poured into water and extracted with DCM. The combined organic layers were washed with brine, dried over $MgSO_4$ and filtered. The filtrate was concentrated under reduced pressure. Purification of the residue on a silica gel column afforded Compound 23-1 or 23-2.

Compound 23-1: $^1$H NMR (400 MHz, $CDCl_3$): δ 2.43 (s, 3H), 3.30-3.63 (m, 37H), 4.00-4.14 (m, 2H), 7.32 (d, J=8.0 Hz, 2H), 7.77 (d, J=8.0 Hz, 2H).

Compound 23-2: $^1$H NMR (400 MHz, $CDCl_3$): δ 2.42 (s, 3H), 3.29-3.79 (m, 61H), 3.99-4.14 (m, 2H), 7.32 (d, J=7.6 Hz, 2H), 7.77 (d, J=7.6 Hz, 2H).

Example 31: Procedures for Preparing NDP-[$CH_2CH(OCH_3)CH_2O$]$_3$—$CH_3$ (Compound 24a), NDT-[$CH_2CH(OCH_3)CH_2O$]$_3$—$CH_3$ (Compound 24b), NDP-[$CH_2CH_2O$]$_n$—[$CH_2CH(OCH_3)CH_2O$]$_3$—$CH_3$ (Compounds 25-1a (n=3) and 25-2a (n=9)), NDT-[$CH_2CH_2O$]$_n$—[$CH_2CH(OCH_3)CH_2O$]$_3$—$CH_3$ (Compounds 25-1b (n=3) and 25-2b (n=9)), NDP-[$CH_2CH(OCH_3)CH_2O$]$_3$—[$CH_2CH_2O$]$_n$—$CH_3$ (Compounds 26-1a (n=3) and 26-2a (n=9)), NDT-[$CH_2CH(OCH_3)CH_2O$]$_3$—[$CH_2CH_2O$]$_n$—$CH_3$ (Compounds 26-1b (n=3) and 26-2b (n=9))

Scheme 6 above shows the preparation of NDP-[$CH_2CH(OCH_3)CH_2O$]$_3$—$CH_3$, NDT-[$CH_2CH(OCH_3)CH_2O$]$_3$—

CH$_3$, NDP-[CH$_2$CH$_2$O]$_n$—[CH$_2$CH(OCH$_3$)CH$_2$O]$_3$—CH$_3$, NDT-[CH$_2$CH$_2$O]$_n$—[CH$_2$CH(OCH$_3$)CH$_2$O]$_3$—CH$_3$, NDP-[CH$_2$CH(OCH$_3$)CH$_2$O]$_3$—[CH$_2$CH$_2$O]$_n$—CH$_3$ or NDT-[CH$_2$CH(OCH$_3$)CH$_2$O]$_3$—[CH$_2$CH$_2$O]$_n$—CH$_3$. NDP or NDT was coupled under basic conditions to provide NDP-[CH$_2$CH(OCH$_3$)CH$_2$O]$_3$—CH$_3$, NDT-[CH$_2$CH(OCH$_3$)CH$_2$O]$_3$—CH$_3$, NDP-[CH$_2$CH$_2$O]$_n$—[CH$_2$CH(OCH$_3$)CH$_2$O]$_3$—CH$_3$, NDT-[CH$_2$CH$_2$O]$_n$—[CH$_2$CH(OCH$_3$)CH$_2$O]$_3$—CH$_3$, NDP-[CH$_2$CH(OCH$_3$)CH$_2$O]$_3$—[CH$_2$CH$_2$O]$_n$—CH$_3$ or NDT-[CH$_2$CH(OCH$_3$)CH$_2$O]$_3$—[CH$_2$CH$_2$O]$_n$—CH$_3$. Compounds 24a, 24b, 25-1a, 25-2a, 25-1b, 25-2b, 26-1a, 26-2a, 26-1b and 26-2b were prepared according to Scheme 6.

Example 32: Preparation of Compound 24a

To a solution of Compound 16 (447 mg, 0.99 mmol) and NDP (486 mg, 1.35 mmol) in acetonitrile (5 mL) was added K$_2$CO$_3$ (685 mg, 4.96 mmol) at room temperature. The solution was stirred at reflux for 22 h and filtered. The filtrate was concentrated under reduced pressure. Purification of the residue on a silica gel column eluted with acetone/DCM (v/v=1:2) and MeOH/DCM (v/v=1:12 and 1:9) afforded Compound 24a (375 mg, 59% yield). $^1$H NMR (400 MHz, CDCl$_3$): δ 1.92 (t, J=6.8 Hz, 2H), 2.42-2.45 (m, 10H), 3.33-3.65 (m, 27H), 3.87 (t, J=6.8 Hz, 2H), 6.82-7.13 (m, 7H).

Example 33: Preparation of Compound 24b

To a solution of Compound 16 (327 mg, 0.726 mmol) and NDT (430 mg, 1.09 mmol) in acetonitrile (5 mL) was added K$_2$CO$_3$ (505 mg, 3.65 mmol) at room temperature. The solution was stirred at reflux for 22 h and filtered. The filtrate was concentrated under reduced pressure. Purification of the residue on a normal phase column eluted with EtOAc/hexane (v/v=3:1) and MeOH/DCM (v/v=1:12 and 1:9) afforded Compound 24b (168 mg, 34% yield). $^1$H NMR (400 MHz, CDCl$_3$): δ 1.91 (t, J=6.8 Hz, 2H), 2.41-2.46 (m, 10H), 3.33-3.65 (m, 27H), 3.92 (t, J=6.8 Hz, 2H), 6.88-7.18 (m, 7H).

Example 34: Preparation of Compound 25-1a

To a solution of Compound 19-1 (607 mg, 1.04 mmol) and NDP (492 mg, 1.37 mmol) in acetonitrile (5 mL) was added K$_2$CO$_3$ (752 mg, 5.44 mmol) at room temperature. The solution was stirred at reflux for 20 h and filtered. The filtrate was concentrated under reduced pressure. Purification of the residue on a silica gel column eluted with acetone/DCM (v/v=2:3) and MeOH/DCM (v/v=1:15, 1:12 and 1:8) afforded Compound 25-1a (550 mg, 68% yield). $^1$H NMR (400 MHz, CDCl$_3$): δ 1.91 (t, J=6.8 Hz, 2H), 2.42-2.57 (m, 10H), 3.33-3.61 (m, 39H), 3.86 (t, J=6.8 Hz, 2H), 6.82-7.14 (m, 7H).

Example 35: Preparation of Compound 25-1b

To a solution of 19-1 (606 mg, 1.04 mmol) and NDT (541 mg, 1.37 mmol) in acetonitrile (5 mL) was added K$_2$CO$_3$ (735 mg, 4.96 mmol) at room temperature. The solution was stirred at reflux for 20 h and filtered. The filtrate was concentrated under reduced pressure. Purification of the residue on a silica gel column eluted with acetone/DCM (v/v=1:2 and 2:3) and MeOH/DCM (v/v=1:12 and 1:8) afforded Compound 25-1b (702 mg, 84% yield). $^1$H NMR (400 MHz, CDCl$_3$): δ 1.91 (t, J=6.8 Hz, 2H), 2.43-2.56 (m, 10H), 3.33-3.65 (m, 39H), 3.92 (t, J=6.8 Hz, 2H), 6.88-7.17 (m, 7H).

Example 36: Preparation of Compound 25-2a

To a solution of Compound 19-2 (898 mg, 1.027 mmol) and NDP (524 mg, 1.456 mmol) in acetonitrile (5 mL) was added K$_2$CO$_3$ (751 mg, 5.433 mmol) at room temperature. The resulting solution was stirred at reflux for 20 h and filtered. The filtrate was concentrated under reduced pressure. Purification of the resulting residue on a silica gel column eluted with acetone/DCM (v/v=1:1) and MeOH/DCM (v/v=1:20, 1:12 and 1:8) afforded Compound 25-2a as colorless oil (738 mg, 69% yield). $^1$H NMR (400 MHz, CDCl$_3$): δ 1.91 (t, J=6.8 Hz, 2H), 2.42-2.56 (m, 10H), 3.33-3.61 (m, 63H), 3.86 (t, J=6.8 Hz, 2H), 6.82-7.14 (m, 7H).

Example 37: Preparation of Compound 25-2b

To a solution of Compound 19-2 (905 mg, 1.035 mmol) and NDT (558 mg, 1.418 mmol) in acetonitrile (5 mL) was added K$_2$CO$_3$ (760 mg, 5.5 mmol) at room temperature. The resulting solution was stirred at reflux for 20 h and filtered. The filtrate was concentrated under reduced pressure. Purification of the resulting residue on a silica gel column eluted with acetone/DCM (v/v=1:2) and MeOH/DCM (v/v=1:15, 1:10 and 1:8) afforded Compound 25-2b as colorless oil (1.01 g, 91% yield). $^1$H NMR (400 MHz, CDCl$_3$): δ 1.91 (t, J=6.4 Hz, 2H), 2.43-2.56 (m, 10H), 3.34-3.62 (m, 63H), 3.92 (t, J=6.8 Hz, 2H), 6.88-7.17 (m, 7H).

Example 38: Preparation of Compound 26-1a

To a solution of Compound 23-1 (1.1 g, 1.89 mmol) and NDP (980 mg, 2.72 mmol) in acetonitrile (10 mL) was added potassium carbonate (1.31 g, 9.48 mmol) at room temperature. The solution was stirred at reflux for 1 day then filtered. The filtrate was concentrated under reduced pressure. Purification of the residue on a silica gel column eluted with acetone/DCM (v/v=1:2 and 1:1) and MeOH/DCM (v/v=1:22, 1:15 and 1:8) afforded Compound 26-1a (711 mg, 49% yield). $^1$H NMR (400 MHz, CDCl$_3$): δ 1.91 (t, J=6.4 Hz, 2H), 2.41-2.45 (m, 10H), 3.33-3.63 (m, 39H), 3.86 (t, J=6.4 Hz, 2H), 6.82-7.12 (m, 7H).

Example 39: Preparation of Compound 26-1b

To a solution of Compound 23-1 (1.3 g, 2.23 mmol) and NDT (1.14 g, 2.90 mmol) in acetonitrile (12 mL) was added K$_2$CO$_3$ (1.55 g, 11.21 mmol) at room temperature. The resulting solution was stirred at reflux for 20 h and filtered. The filtrate was concentrated under reduced pressure. Purification of the residue on a silica gel column eluted with EtOAc/hexane (v/v=3:1), acetone/DCM (v/v=1:2) and MeOH/DCM (v/v=1:15 and 1:8) afforded Compound 26-1b (649 mg, 36% yield). $^1$H NMR (400 MHz, CDCl$_3$): δ 1.91 (t, J=6.4 Hz, 2H), 2.42-2.44 (m, 10H), 3.33-3.63 (m, 39H), 3.92 (t, J=6.4 Hz, 2H), 6.88-7.18 (m, 7H).

Example 40: Preparation of Compound 26-2a

To a solution of Compound 23-2 (1.1 g, 1.3 mmol) and NDP (688 mg, 2.90 mmol) in acetonitrile (7 mL) was added K$_2$CO$_3$ (898 mg, 6.5 mmol) at room temperature. The resulting solution was stirred at reflux for 1 day and filtered.

The filtrate was concentrated under reduced pressure. Purification of the residue by a silica gel column eluted with acetone/DCM (v/v=1:1 and MeOH/DCM (v/v=1:20, 1:12 and 1:8) afforded Compound 26-2a (564 mg, 42% yield). $^1$H NMR (400 MHz, CDCl$_3$): δ 1.91 (t, J=6.4 Hz, 2H), 2.43-2.56 (m, 10H), 3.33-3.62 (m, 63H), 3.86 (t, J=6.4 Hz, 2H), 6.82-7.13 (m, 7H).

Example 41: Preparation of Compound 26-2b

To a solution of 23-2 (1.14 g, 1.346 mmol) and NDT (737 mg, 2.0 mmol) in acetonitrile (7 mL) was added K$_2$CO$_3$ (930 mg, 6.7 mmol) at room temperature. The resulting solution was stirred at reflux for 1 day and filtered. The filtrate was concentrated under reduced pressure. Purification of the residue on a silica gel column eluted with acetone/DCM (v/v=1:1) and MeOH/DCM (v/v=1:20, 1:12 and 1:8) afforded Compound 26-2b (623 mg, 43% yield). $^1$H NMR (400 MHz, CDCl$_3$): δ 1.92 (t, J=6.4 Hz, 2H), 2.43-2.56 (m, 10H), 3.33-3.62 (m, 63H), 3.93 (t, J=6.4 Hz, 2H), 6.88-7.16 (m, 7H).

Example 42: Procedures for Preparing NDP-[CH$_2$CH(OH)CH$_2$O]$_3$—H (Compound 33a), NDT-[CH$_2$CH(OH)CH$_2$O]$_3$—H (Compound 33b)

Scheme 7 above shows the preparation of Compounds 33a and 33b. Benzyl protected triglycerol was mono protected with THP to provide Compound 28. Compound 28 was further protected to provide Compound 29. The THP was removed under standard protocol to provide Compound 30, which was subsequently tosylated to provide Compound 31. Global deprotection was accomplished with H2 and Pd/C to provide Compound 32. Compound 32 was coupled with NDP or NDT under basic conditions to provide Compound 33a or Compound 33b.

Example 43: Preparation of Compound 27 [2,6,10-Tris(benzyloxy)-4,8-dioxaundecane-1,11-diol]

Compound 27 was prepared from Compound 7 according to a published procedure (Hamada, M. et al., *Synthesis*. 2008, 22, 3663-3669). $^1$H NMR (400 MHz, CDCl$_3$): δ 2.25 (br, 2H), 3.56-3.72 (m, 15H), 4.54-4.70 (m, 6H), 7.25-7.38 (m, 15H).

Example 44: Preparation of Compound 28

To a solution of Compound 27 (9.50 g, 18.6 mmol) and pTSA (0.586 g, 3.08 mmol) in DCM (120 mL) was added slowly 3,4-dihydro-2H-pyran (1.40 mL, 15.4 mmol) in DCM (30 mL) at 0° C. and the reaction mixture was stirred at room temperature for 18 h. The reaction mixture was diluted with water and DCM. The aqueous layer was extracted with DCM (150 mL×3) and the combined organic layers were washed with brine and dried over MgSO$_4$. The drying agent was removed by filtration and the solvent was evaporated under reduced pressure. Purification of the residue by a silica gel column eluted with hexane/EtOAc (v/v=2:1, 1:1 and 1:4), EtOAc/Acetone (v/v=4:1) and DCM/MeOH (v/v=9:1) afforded Compound 28 (5.18 g, 57%). $^1$H NMR (CDCl$_3$, 400 MHz): δ 1.47-1.58 (m, 4H), 1.65-1.69 (m, 4H), 1.79 (d, J=9.6 Hz, 4H), 3.44-3.59 (m, 11H), 3.72-3.84 (m, 8H), 4.45 (s, 2H), 4.66 (s, 6H), 7.23-7.34 (m, 15H).

Example 45: Preparation of Compound 29

To a solution of Compound 28 (5.18 g, 8.71 mmol) in THF (60 mL) was added sodium hydride (0.871 g, 21.8 mmol) at 0° C. and the reaction mixture was stirred for 30 minutes at room temperature. To the suspension was added slowly benzyl bromide (1.35 mL, 11.3 mmol). The reaction mixture was stirred at room temperature for 20 h. The reaction was quenched with water and diluted with DCM. The aqueous layer was extracted with DCM (100 mL×3) and the combined organic layers were washed with brine and dried over MgSO$_4$. The drying agent was removed by filtration and the solvent was evaporated under reduced pressure. Purification of the residue on a silica gel column eluted with hexane/EtOAc (v/v=5:1, 3:1, and 1:1) afforded Compound 29 (5.59 g, 94%): $^1$H NMR (400 MHz, CDCl$_3$) δ 1.41-1.82 (m, 6H), 3.40-3.90 (m, 17H), 4.50-4.52 (m, 2H), 4.57-4.60 (m, 1H), 4.65-4.70 (m, 6H), 7.20-7.38 (m, 20H).

Example 46: Preparation of Compound 30

To a solution of Compound 29 (5.58 g, 8.15 mmol) in MeOH (55 mL) was added pTSA (0.155 g, 0.815 mmol) at room temperature and the reaction mixture was stirred at room temperature for 18 h. The reaction mixture was quenched with sat. NaHCO$_{3(aq)}$ and extracted with DCM (60 mL×3). The combined organic layers were washed with brine and dried over MgSO$_4$. The drying agent was removed by filtration and the solvent was evaporated under reduced pressure to afford Compound 30 (4.87 g, 99%): $^1$H NMR (400 MHz, CDCl$_3$) δ 2.12-2.20 (m, 1H), 3.40-3.80 (m, 15H), 4.50-4.80 (m, 8H), 7.20-7.38 (m, 20H).

Example 47: Preparation of Compound 31

To a solution of Compound 30 (4.86 g, 8.09 mmol) in DCM (25 mL) was added tosyl chloride (2.31 g, 12.1 mmol) and potassium hydroxide (1.82 g, 32.4 mmol) at 0° C. and the reaction mixture was stirred at room temperature for 18 h. The reaction mixture was diluted with DCM (100 mL) and H$_2$O (80 mL). The aqueous layer was separated and extracted with DCM (100 mL×2). The combined organic layers were washed with brine and dried over MgSO$_4$. The drying agent was removed by filtration and the solvent was evaporated under reduced pressure. Purification of the residue by a silica gel column eluted with Hexanes/EtOAc (v/v=4:1, 3:1 and 2:1) afforded Compound 31 as colorless oil (5.31 g, 87% yield): $^1$H NMR (400 MHz, CDCl$_3$) δ 2.38 (s, 3H), 3.40-3.80 (m, 13H), 4.00-4.10 (m, 1H), 4.10-4.20 (m, 1H), 4.40-4.80 (m, 8H), 7.20-7.38 (m, 22H), 7.73 (d, J=8.0 Hz, 2H).

Example 48: Preparation of Compound 32

To a solution of Compound 31 (0.573 g, 0.759 mmol) in MeOH (5 mL) was added Pd/C (0.081 g, 0.076 mmol) at room temperature and the reaction mixture was stirred at room temperature under H2 (1 atm) for 22 h. The reaction was diluted with MeOH and filtered. The solvent was evaporated under reduced pressure to afford Compound 32 (299 mg, quant.): $^1$H NMR (400 MHz, CDCl$_3$) δ 2.20 (brs, 3H), 2.42 (s, 3H), 3.40-4.10 (m, 15H), 4.55 (brs, 1H), 7.33 (d, J=8.0 Hz, 2H), 7.76 (d, J=8.0 Hz, 2H).

Example 49: Preparation of Compound 33a

To a stirred solution of NDP (0.355 g, 0.987 mmol) and Compound 32 (0.284 g, 0.720 mmol) in acetonitrile (4 mL) was added K$_2$CO$_3$ (0.525 g, 3.80 mmol) at room temperature under argon. The reaction mixture was refluxed for 18 h, diluted with DCM and filtered. The solvent was evaporated under reduced pressure. Purification of the residue on a silica gel column eluted with EtOAc/MeOH (v/v=2:1, and 1:1) afforded Compound 33a (243 mg, 58% yield): $^1$H NMR (400 MHz, CDCl$_3$) δ 1.89 (t, J=6.4 Hz, 2H), 2.20-2.50 (m, 14H), 3.30-4.00 (m, 17H), 6.82-7.14 (m, 7H).

Example 50: Preparation of Compound 33b

To a stirred solution of NDT (0.550 g, 1.40 mmol) and Compound 32 (0.424 g, 1.07 mmol) in acetonitrile (8 mL) was added K$_2$CO$_3$ (0.739 g, 5.35 mmol) at room temperature under argon. The reaction mixture was refluxed for 20 h, diluted with acetone, filtered and washed with DCM. The solvent was evaporated under reduced pressure. Purification of the residue on a silica gel column eluted with EtOAc/MeOH (v/v=2:1 and 1:1) afforded Compound 33b (310 mg, 47% yield): $^1$H NMR (400 MHz, CDCl$_3$) δ 1.90 (t, J=6.8 Hz, 2H), 2.20-2.50 (m, 14H), 3.36-3.90 (m, 15H), 3.93 (t, J=6.8 Hz, 2H), 6.87-7.17 (m, 7H).

Example 51: Cell Culture and Chemicals

Human non-small cell lung cancer (NSCLC) cell lines (e.g., A549, H441GL and H1299), colon cancer cell lines (e.g., HCT116 and DLD1), breast cancer cell lines (e.g., MCF7 and MDA-MB-231), and pancreatic cancer cell lines (e.g., PANC-1 and SUIT-2) were used in cytotoxicity studies. These NSCLC cell lines have intrinsic resistance to epidermal growth factor receptor (EGFR) inhibitors, e.g., gefitinib. A549 and H441GL are EGFR-wild type adenocarcinoma cell lines. H1299 is an EGFR-wild type large cell carcinoma cell line. HCT116 and DLD1 are metastatic colon cell lines. MCF7 is a hormone-responsive breast cancer cell line. MDA-MB-231 is a triple-negative breast cancer cell line. PANC-1 is a metastatic adenocarcinoma cell line. SUIT-2 is a pancreatic ductal adenocarcinoma cell line.

All cell lines were grown and maintained in RPMI medium supplemented with 10% fetal bovine serum (FBS, Invitrogen), 2 mM L-glutamine, 100 U/mL penicillin, and 100 μg/mL streptomycin. For cell the culture experiment, stock solution (10 mM) of each test compound was dissolved in dimethyl sulfoxide (DMSO; Sigma).

Example 52: Cytotoxicity and Sulforhodamine B Assay

Cells were plated in 96-well plates at a density of 2000 cells per well in triplicate. The cells in each well were treated on the third day (to ensure proper plating efficiency and vitality) with different concentrations (0-50 μM) of each test compound for 48 h.

Cell viability was assessed using the sulforhodamine B (SRB) assay. The medium was discarded, and the adherent cells were fixed by 100 μL of cold 10% trichloroacetic acid (w/v) in each well for 1 h at 4° C. After fixation, cells were stained with 100 μL/well of 0.4% (w/v, in 1% acetic acid) SRB solution for 30 min at room temperature, and then washed 5 times with 1% acetic acid. After air-drying, 100 μL of 10 mM Tris base was added to each well and the absorbance was read at 530 nm. Cytotoxicity is expressed as the percent of cells in drug treated wells relative to number of cells in the solvent only control (set to 100%). Each experiment was performed independently in triplicate and cytotoxicity IC$_{50}$ value of each test compound was calculated from cytotoxicity data obtained at various concentrations.

The cytotoxicity values (IC$_{50}$) of NDP and NDT oligomer conjugates are shown in Table 2 and Table 3.

TABLE 2

| Compound No. | IC$_{50}$ (μM) | | |
|---|---|---|---|
| | H441GL | A549 | H1299 |
| PCP | 12.9 | 14.6 | 28.7 |
| NDP | 8.4 | 9.7 | 6.6 |
| 5-1a | 16.0 | 15.7 | — |
| 5-2a | 18.7 | 25.2 | — |
| 5-3a | 3.0 | 2.7 | — |
| 5-4a | 3.0 | 6.2 | — |
| TFP | 21.6 | 23.5 | 28.7 |
| NDT | 3.9 | 6.3 | 6.9 |
| 5-1b | 3.2 | 3.8 | — |
| 5-2b | 2.7 | 3.2 | — |
| 5-3b | 1.6 | 2.7 | — |
| 5-4b | 17.5 | 13.8 | — |
| 4-1a | 13.2 | 32.5 | — |
| 4-2a | 9.1 | 10.9 | — |
| 4-3a | 12.7 | 11.9 | — |
| 4-4a | 12.9 | 20.2 | — |
| 4-1b | 10.5 | 26.3 | — |
| 4-2b | 6.8 | 21.3 | — |
| 4-3b | 10.5 | 11.5 | — |
| 4-4b | 36.4 | NA | — |
| 6-1a | 21.5 | 25.8 | — |
| 6-2a | 25.2 | 31.5 | — |
| 6-3a | 24.3 | 22.3 | — |
| 6-4a | 39.1 | NA | — |
| 6-1b | 16.2 | 17.0 | — |
| 6-2b | 15.5 | 15.5 | — |
| 6-3b | N.A. | 20.6 | — |
| 6-4b | 30.0 | 44.2 | — |
| 24a | 19.1 | 11.7 | 14.2 |
| 24b | 21.0 | 11.8 | 10.9 |
| 25-1a | 13.3 | 12.7 | 13.1 |
| 25-1b | 8.8 | 11.4 | 6.9 |
| 25-2a | 17.5 | 16.7 | 16.8 |
| 25-2b | 11.4 | 14.0 | 13.9 |
| 26-1a | 12.1 | 11.2 | 24.9 |
| 26-1b | 12.1 | 14.4 | 20.4 |
| 26-2a | 25.4 | 23.8 | 42.6 |
| 26-2b | 12.1 | 15.6 | 25.3 |
| 33a | 25.0 | 35.2 | 28.4 |
| 33b | 17.9 | 19.8 | 20.8 |

TABLE 3

| Cell Line | Tissue | IC50 (μM) | | | | | | | | | | | |
|---|---|---|---|---|---|---|---|---|---|---|---|---|---|
| | | 4-1a | 4-2a | 4-3a | 5-1a | 5-2a | 5-3a | 4-1b | 4-2b | 4-3b | 5-1b | 5-2b | 5-3b |
| HCT116 | Colon | — | — | — | — | — | — | 6.5 | 6.5 | 8.4 | 10.0 | 7.3 | 7.9 |
| DLD1 | Colon | — | — | — | — | — | — | 8.0 | 13.9 | 18.0 | 35.9 | 15.2 | 18.2 |
| MCF7 | Breast | 12.8 | 13.2 | 10.0 | 15.5 | 15.3 | 6.5 | 13.1 | 13.2 | 10.2 | 13.6 | 12.0 | 8.3 |
| MDA-MB-231 | Breast | 11.9 | 18.1 | 15.6 | 22.2 | 21.6 | 8.9 | 14.7 | 15.8 | 13.8 | 21.6 | 15.8 | 9.2 |
| PANC-1 | Pancreas | 12.3 | 13.1 | 7.1 | 6.7 | 6.9 | 5.0 | 20.0 | 10.5 | 15.2 | 18.2 | 12.5 | 3.6 |
| SUIT-2 | Pancreas | 13.2 | 13.5 | 25.4 | 18.6 | 16.2 | 11.3 | 13.3 | 15.6 | 22.0 | 21.4 | 10.8 | 10.8 |

TABLE 3-continued

| Cell Line | Tissue | 24a | 24b | 25-1a | 25-1b | 25-2a | 25-2b | 26-1a | 26-1b | 26-2a | 26-2b | 33a | 33b |
|---|---|---|---|---|---|---|---|---|---|---|---|---|---|
| | | IC50 ($\mu$M) | | | | | | | | | | | |
| HCT116 | Colon | — | 5.9 | — | 7.2 | — | 11.4 | 11.2 | 8.5 | 13.3 | 8.9 | 20.2 | 14.9 |
| DLD1 | Colon | — | 11.8 | — | 11.7 | — | 15.3 | 22.3 | 13.9 | 32.8 | 19.2 | 35.2 | 26.4 |
| MCF7 | Breast | 14.5 | 9.9 | 14.6 | 12.2 | 13.3 | 10.9 | 14.6 | 10.3 | 24.2 | 10.0 | 26.0 | 13.8 |
| MDA-MB-231 | Breast | 17.6 | 11.3 | 12.7 | 11.2 | 16.8 | 13.1 | 13.5 | 6.4 | 16.3 | 12.5 | 24.2 | 14.8 |
| PANC-1 | Pancreas | 12.4 | 25.8 | 16.4 | 10.0 | 35.4 | 2.9 | 15.8 | NA | 27.9 | 12.9 | 30.2 | 23.5 |
| SUIT-2 | Pancreas | 16.1 | 13.9 | 13.0 | 10.9 | 25.6 | 13.0 | 25.8 | 12.9 | 26.9 | 17.2 | 34.0 | 25.7 |

Table 2 shows that PCP, TFP, NDP, NDT, —[CH$_2$CH$_2$O]$_n$—CH$_3$ carbamate conjugates of NDP and NDT (Compounds 5-1a, 5-2a, 5-3a, 5-4a, 5-1b, 5-2b, 5-3b and 5-4b), —[CH$_2$CH$_2$O]$_n$—CH$_3$ PEGylated conjugates of NDP and NDT (Compounds 4-1a, 4-2a, 4-3a, 4-4a, 4-1b, 4-2b and 4-3b), —COCH$_2$[CH$_2$CH$_2$O]$_n$—CH$_3$ amide conjugates of NDP and NDT (Compounds 6-1a, 6-2a, 6-3a, 6-1b and 6-2b), NDP-[CH$_2$CH(OCH$_3$)CH$_2$O]$_3$—CH$_3$ (Compound 24a), NDT-[CH$_2$CH(OCH$_3$)CH$_2$O]$_3$—CH$_3$ (Compound 24b), NDP-[CH$_2$CH$_2$O]$_n$—[CH$_2$CH(OCH$_3$)CH$_2$O]$_3$—CH$_3$ (Compounds 25-1a (n=3) and 25-2a (n=9)), NDT-[CH$_2$CH$_2$O]$_n$—[CH$_2$CH(OCH$_3$)CH$_2$O]$_3$—CH$_3$ (Compounds 25-1b (n=3) and 25-2b (n=9)), NDP-[CH$_2$CH(OCH$_3$)CH$_2$O]$_3$—[CH$_2$CH$_2$O]$_n$—CH$_3$ (Compounds 26-1a (n=3) and 26-2a (n=9)), NDT-[CH$_2$CH(OCH$_3$)CH$_2$O]$_3$—[CH$_2$CH$_2$O]$_n$—CH$_3$ [Compounds 26-1b (n=3) and 26-2b (n=9)], NDP-[CH$_2$CH(OH)CH$_2$O]$_3$—H (Compound 33a) and NDT-[CH$_2$CH(OH)CH$_2$O]$_3$—H (Compound 33b) inhibit cell proliferation of lung cancer cells. NA indicates no activity.

The data in Table 3 indicate that almost all of the conjugates of NDP and NDT tested inhibit cell proliferation of various cancer cells.

Example 53: In Vivo Examination of Anti-Lung Cancer Effects Mediated by Test Compounds As shown in Study 1 and Study 2, test-compound treatment suppressed tumorigenesis of gefitinib-resistant H441 in a mouse lung cancer model.

Study 1

H441GL cells (1×10$^6$ cells in 100 $\mu$L phosphate-buffered saline/injection) were subcutaneously injected into the right flank of NOD/SCID mice (female, 4-6 weeks old). Mice were allowed 2 weeks for tumor growth. On the first day of Week 3 post injection, tumor-bearing mice were randomly divided into control group (DMSO vehicle, intraperitoneal (i.p.) injection) and test compound treatment groups (5 mg/kg/day, 5 days/week, i.p. injection). Over the period of 10 weeks, tumorigenesis in both groups was measured using a caliper on a weekly basis. The change in tumor size was expressed as in fold change from Week 3. In this study body weight of each mouse was also recorded at the end of each study week.

The results of the effect of compounds on tumor size in mouse studies are summarized in Table 4. As shown in Table 4, all of the test compounds suppressed and delayed the growth of the tumor as compared to the vehicle control. Among these compounds, Compound 5-2b had the largest effect of suppressing tumor growth. Also, the body weights of test compound-treated mice were not significantly different from the control group (data not shown).

TABLE 4

| | Tumor Size [Fold Change from Week 3 (Mean ± SD, n = 4)] | | |
|---|---|---|---|
| Compound, i.p. | Week 3 | Week 9 | Week 13 |
| Control | 1 ± 0 | 38.4 ± 8.8 | 100.6 ± 26.7 |
| 5-1a | 1 ± 0 | 24.9 ± 4.3 | 55.4 ± 10.8 |
| 5-1b | 1 ± 0 | 28.2 ± 7.4 | 69.8 ± 18.4 |
| 5-2a | 1 ± 0 | 28.0 ± 6.5 | 66.2 ± 18.4 |
| 5-2b | 1 ± 0 | 23.4 ± 7.5 | 51.6 ± 17.6 |
| 5-3a | 1 ± 0 | 23.7 ± 3.4 | 53.9 ± 10.1 |
| 5-3b | 1 ± 0 | 33.4 ± 8.2 | 79.4 ± 20.3 |

Study 2

A mouse study similar to Study 1 was conducted to evaluate compounds listed in Table 5. In this study, the daily dose was 0.0127 mmol/kg instead of 5 mg/kg. The results of the effect of compounds on tumor size in mouse studies are summarized in Table 5. As shown in Table 5, all of the test compounds suppressed and delayed the growth of the tumor as compared to the vehicle control by Week 13. Among these compounds, Compound 4-2b had the largest effect of suppressing tumor growth. Also, the body weights of test compound-treated mice were not significantly different from the control group (data not shown).

TABLE 5

| | Tumor Size [Fold Change from Week 3 (Mean ± SD, n = 4)] | | |
|---|---|---|---|
| Compound, i.p. | Week 3 | Week 9 | Week 13 |
| Control | 1 ± 0 | 13.2 ± 1.8 | 39.8 ± 6.5 |
| 4-2a | 1 ± 0 | 10.3 ± 1.6 | 25.6 ± 5.1 |
| 4-2b | 1 ± 0 | 9.4 ± 2.6 | 23.3 ± 6.2 |
| 4-3a | 1 ± 0 | 12.5 ± 1.5 | 32.6 ± 4.3 |
| 4-3b | 1 ± 0 | 11.7 ± 2.1 | 30.2 ± 6.2 |
| 25-1a | 1 ± 0 | 12.3 ± 2.0 | 31.5 ± 5.4 |
| 25-1b | 1 ± 0 | 10.2 ± 1.4 | 25.0 ± 4.4 |
| 25-2b | 1 ± 0 | 13.0 ± 1.6 | 35.7 ± 5.3 |

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A method of treating non-small cell lung cancer (NSCLC), comprising administering to a subject in need thereof a therapeutically effective amount of a compound of Formula (I):

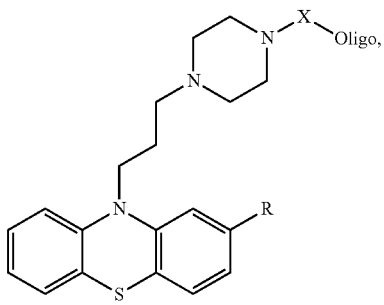

(I)

or a pharmaceutically acceptable salt thereof, wherein:

Oligo is an oligomer or a co-oligomer selected from the group consisting of —[CH$_2$CH(OR$^1$)CH$_2$O]$_m$—R$^2$, —[CH$_2$CH$_2$O]$_n$—R$^3$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$;

R is H, halo, C$_1$-C$_4$ alkyl substituted with one or more halo, or —S—C$_1$-C$_4$ alkyl;

each of R$^1$, R$^2$ and R$^3$ independently is H or C$_1$-C$_4$ alkyl;

X is a bond, C(O), C(O)O, or C(O)CH$_2$O;

m is an integer ranging from 2 to 16, and n is an integer ranging from 3 to 16.

2. The method of claim 1, wherein the non-small cell lung cancer is adenocarcinoma, squamous cell carcinoma, or large cell carcinoma.

3. The method of claim 1, wherein the non-small cell lung cancer is resistant or refractory to at least one prior therapy.

4. The method of claim 3, wherein the non-small cell lung cancer is resistant to chemotherapy.

5. The method of claim 4, wherein the non-small cell lung cancer is resistant to epidermal growth factor receptor-tyrosine kinase inhibitors (EGFR-TKI).

6. The method of claim 1, wherein the non-small cell lung cancer expresses cancer stem-like cells (CSC).

7. The method of claim 1, further comprising administering to the subject an additional anti-cancer agent.

8. The method of claim 7, wherein the additional anti-cancer agent is cisplatin, gefitinib, or a combination thereof.

9. The method of claim 1, wherein Oligo is an oligomer or a co-oligomer selected from the group consisting of —[CH$_2$CH(OR$^1$)CH$_2$O]$_m$—R$^2$, —[CH$_2$CH(OR$^1$)CH$_2$O]$_m$—[CH$_2$CH$_2$O]$_n$—R$^2$, and —[CH$_2$CH$_2$O]$_n$—[CH$_2$CH(OR$^1$)CH$_2$O]$_m$—R$^2$.

10. The method of claim 1, wherein Oligo is —[CH$_2$CH(OR$^1$)CH$_2$O]$_m$—R$^2$.

11. The method of claim 1, wherein Oligo is a co-oligomer selected from —[CH$_2$CH(OR$^1$)CH$_2$O]$_m$—[CH$_2$CH$_2$O]$_n$—R$^2$ and —[CH$_2$CH$_2$O]$_n$—[CH$_2$CH(OR$^1$)CH$_2$O]$_m$—R$^2$.

12. The method of claim 1, wherein:
Oligo is —[CH$_2$CH$_2$O]$_n$—R$^3$;
X is a bond; and
n is 6, 7, 8, 9, 10, 11, 14, 15, or 16.

13. The method of claim 1, wherein X is C(O), C(O)O, or C(O)CH$_2$O.

14. The method of claim 1, wherein R is halo or C$_1$-C$_4$ alkyl substituted with one or more F.

15. The method of claim 1, wherein R is C$_1$, CF$_3$, SCH$_3$, or H.

16. The method of claim 1, wherein each R$^1$ independently is H or methyl.

17. The method of claim 1, wherein R$^2$ is H or methyl.

18. The method of claim 1, wherein R$^3$ is H or methyl.

19. The method of claim 1, wherein the compound is selected from:

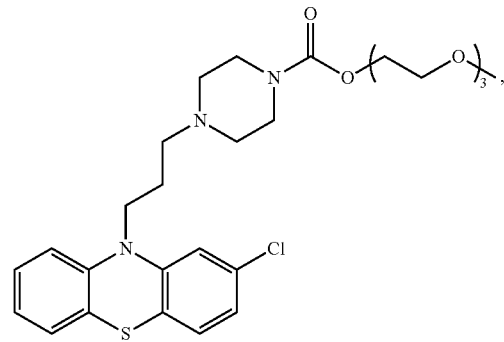

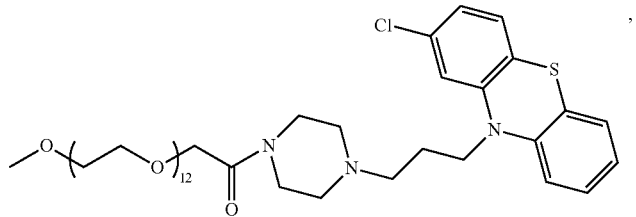

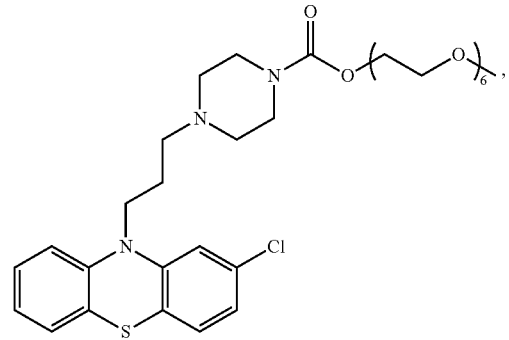

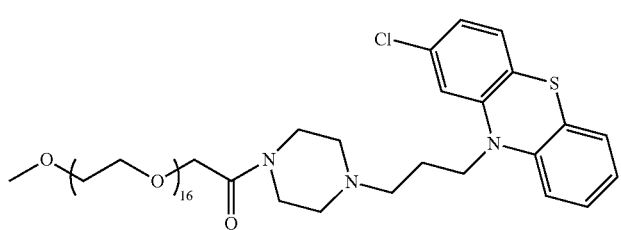

-continued
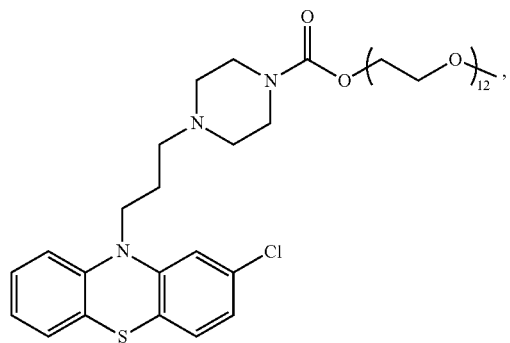
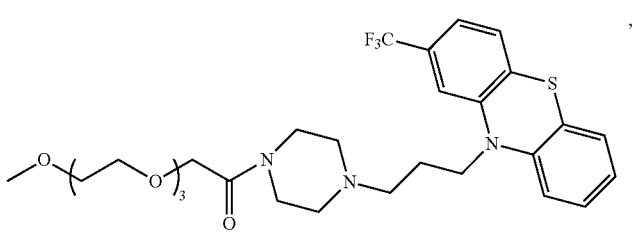
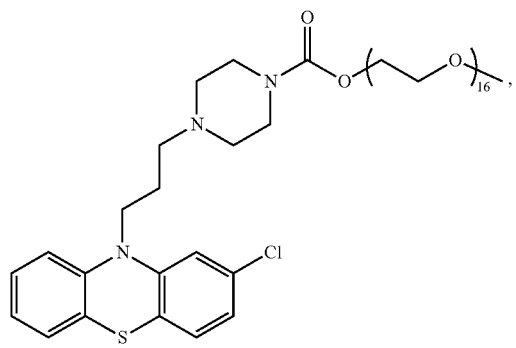
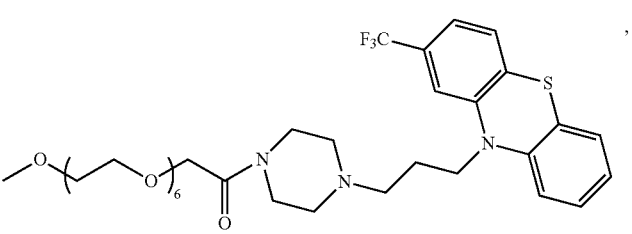
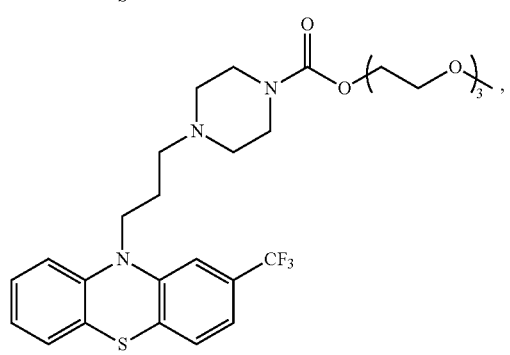
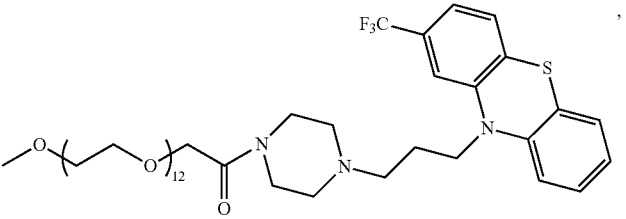
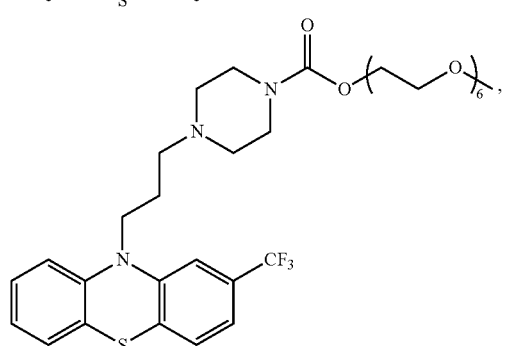
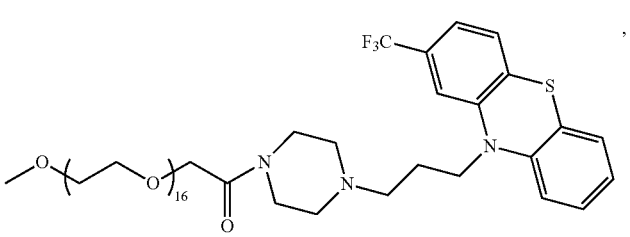
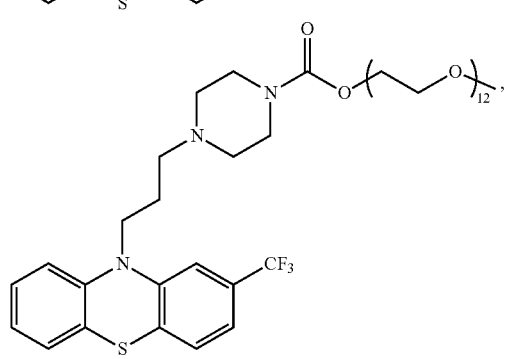

-continued
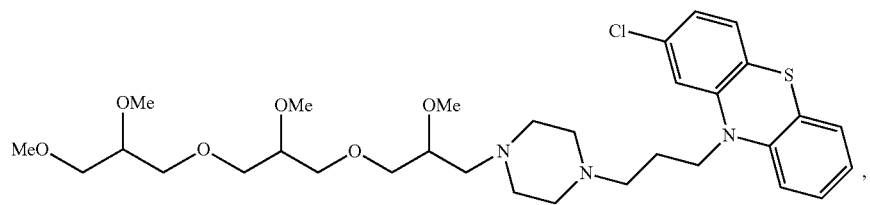
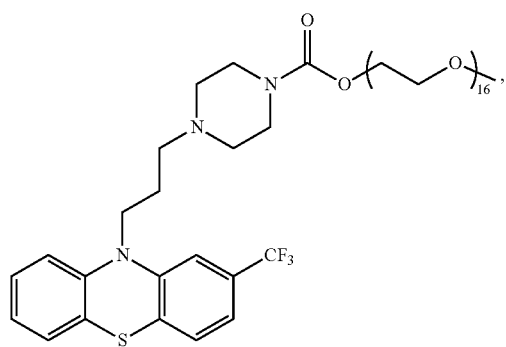
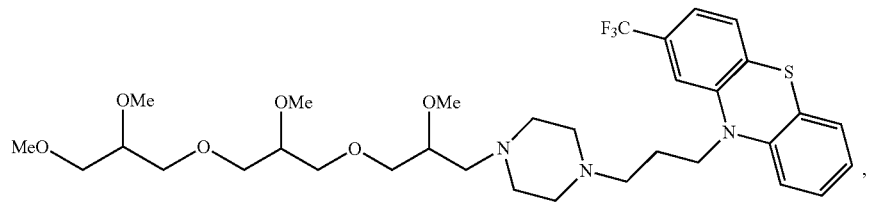
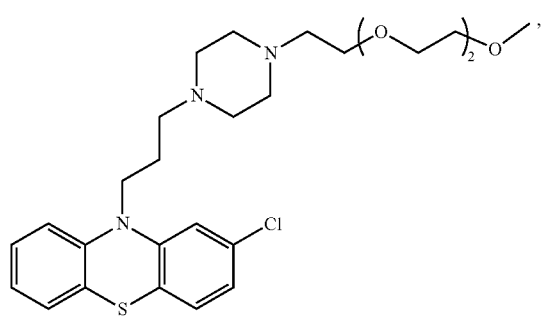
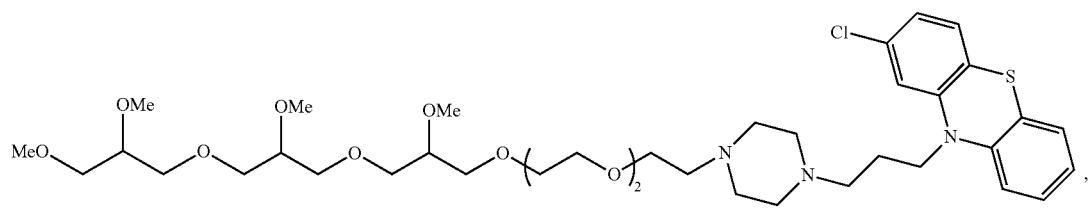
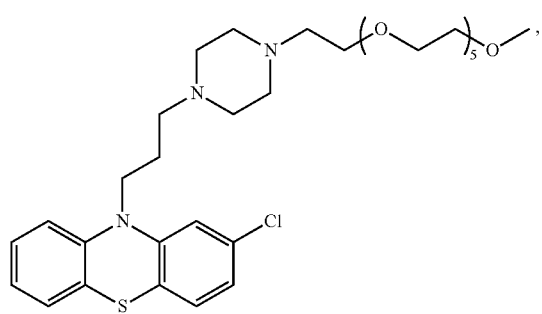

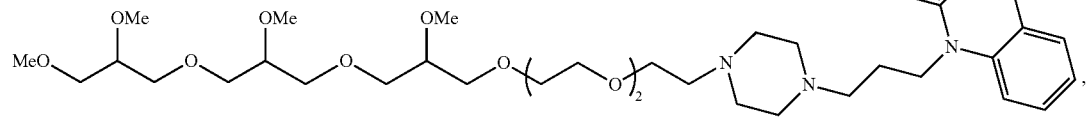
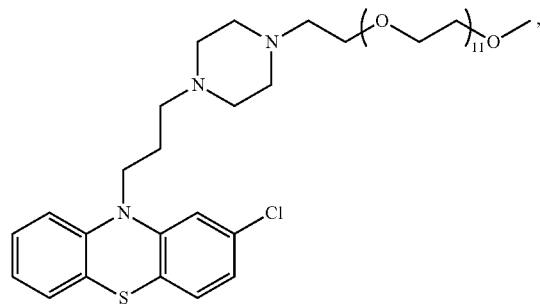
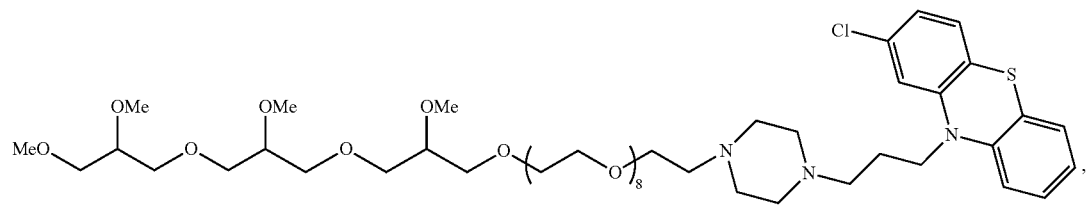
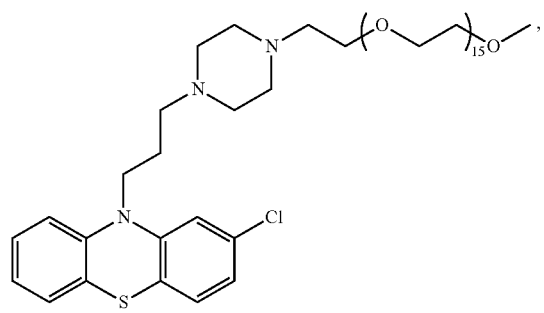
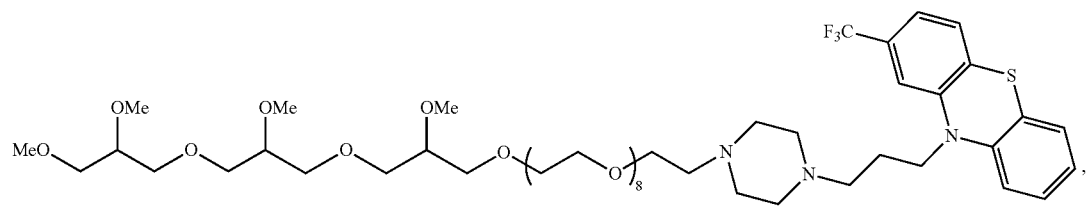
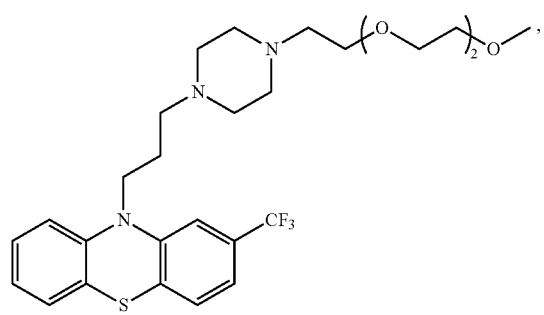

-continued
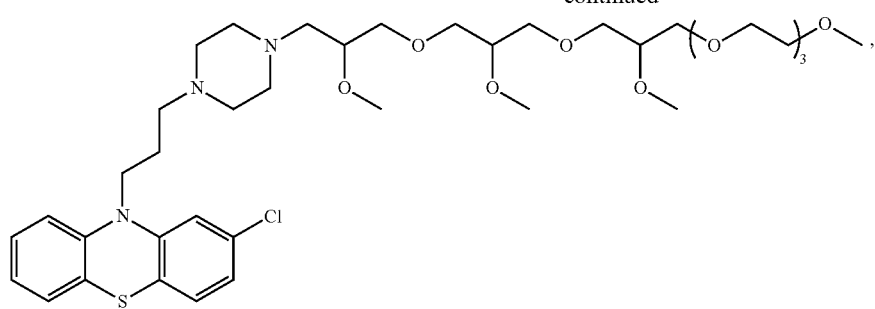
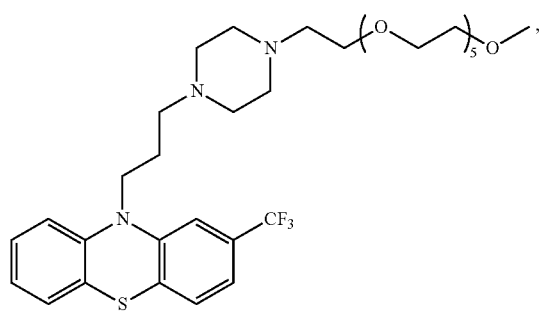
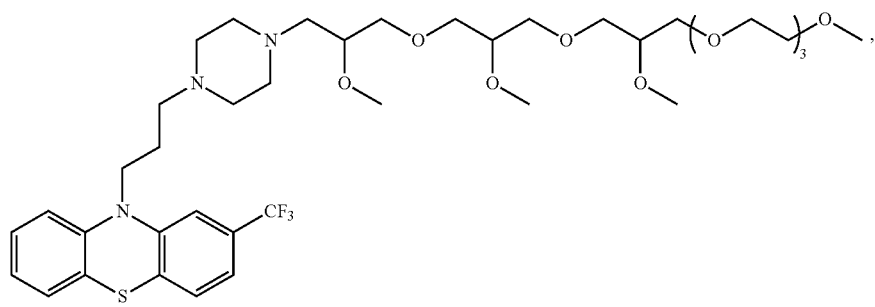
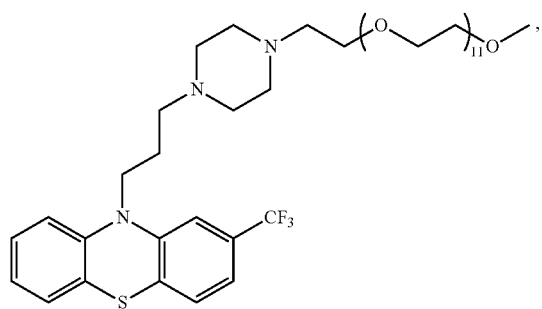
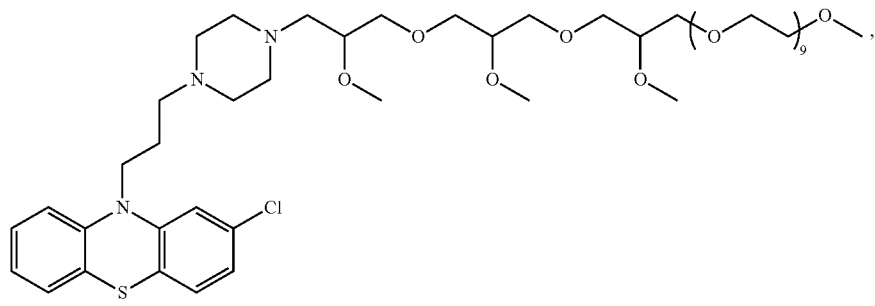

-continued
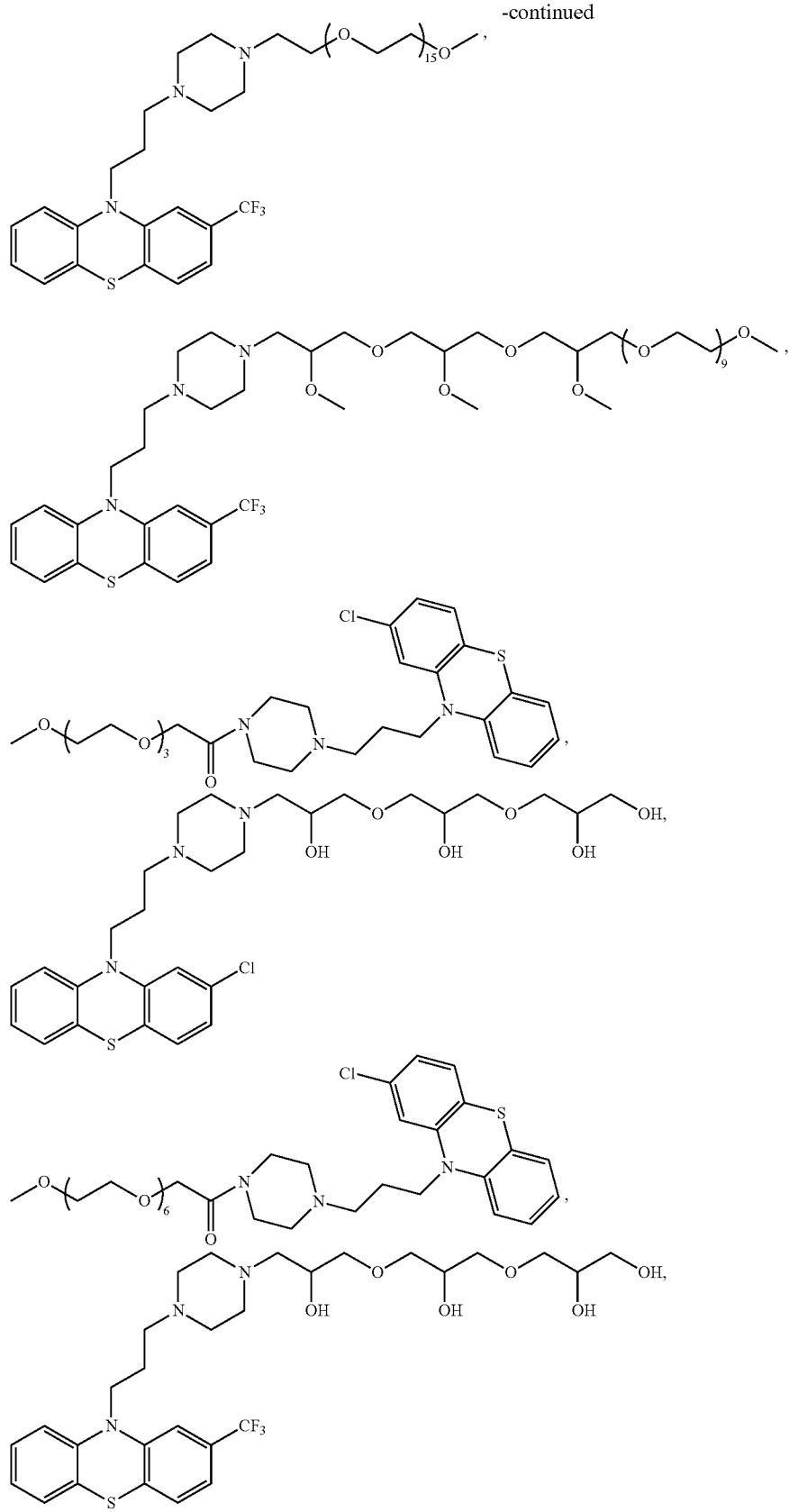
and pharmaceutically acceptable salts thereof.

20. The method of claim 1, wherein the compound is selected from:
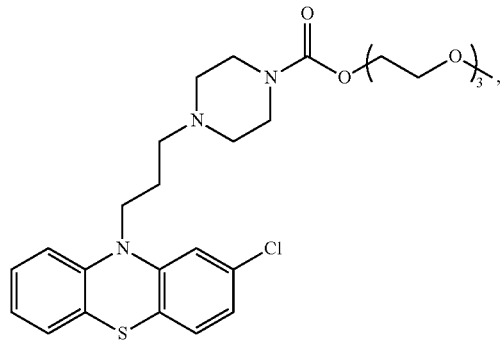
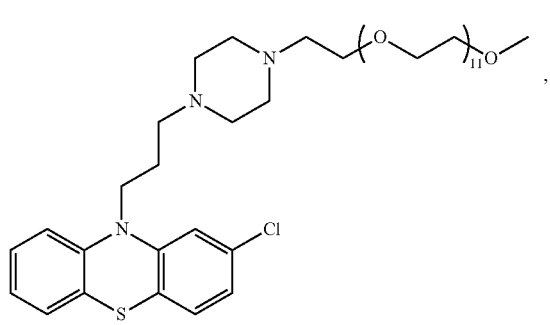
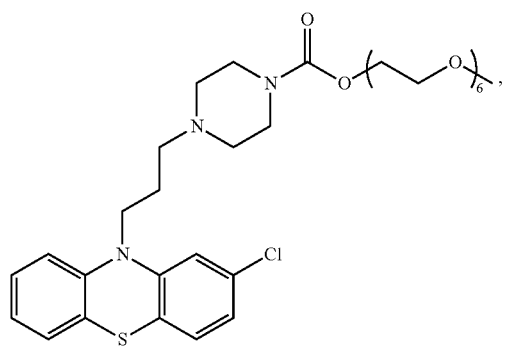
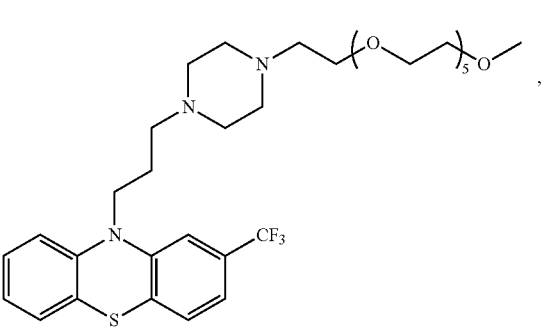
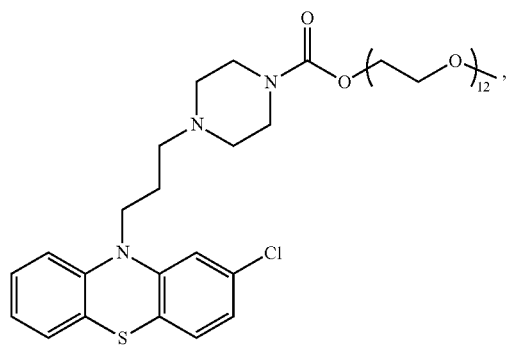
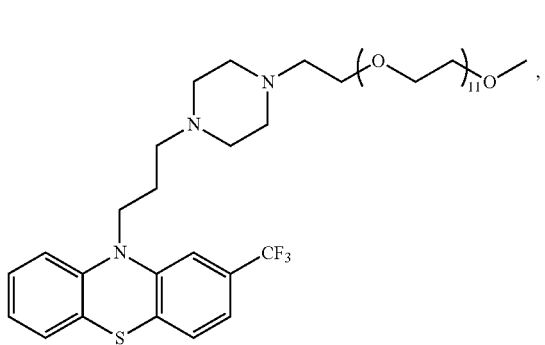
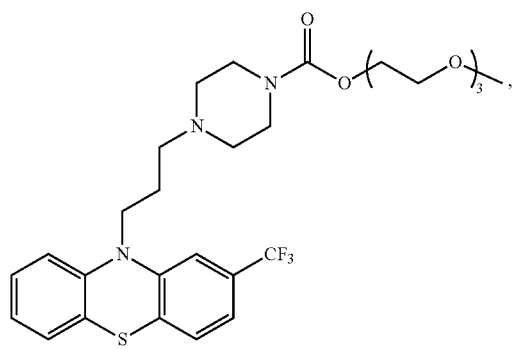
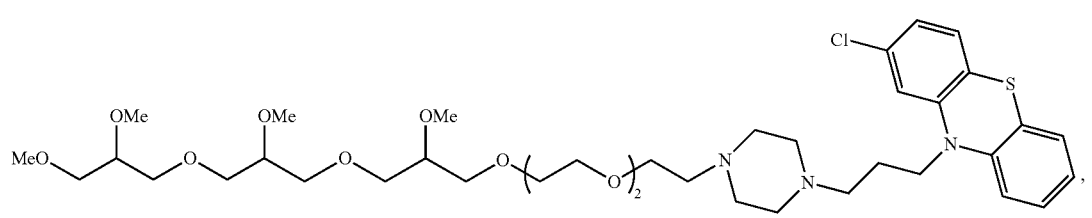

-continued
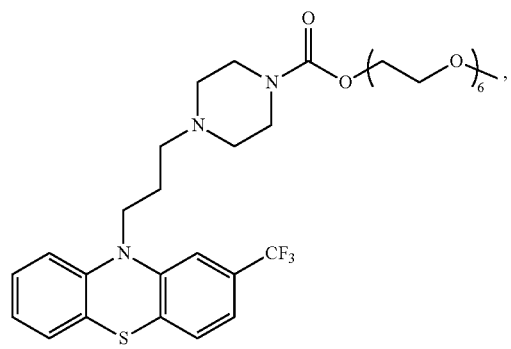
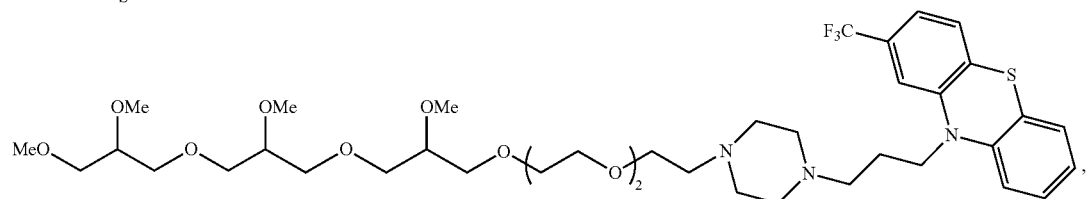
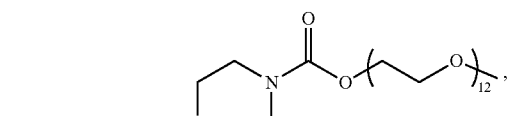
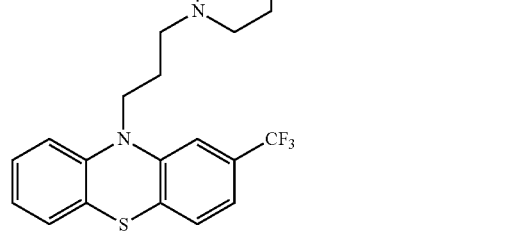
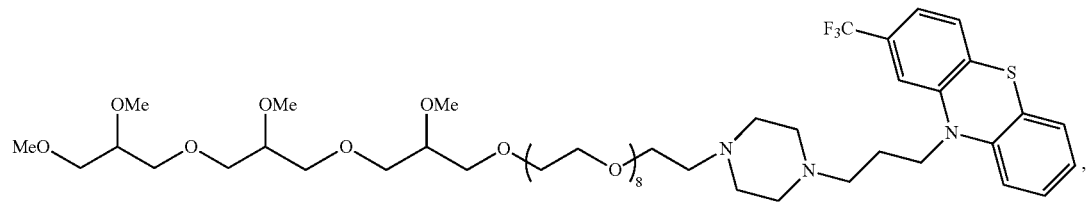
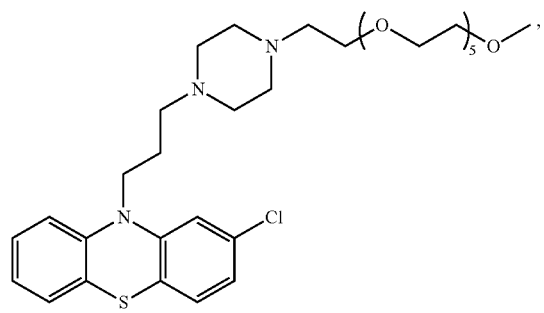
and pharmaceutically acceptable salts thereof.
* * * * *